US012668847B2

(12) United States Patent
Mande et al.

(10) Patent No.: US 12,668,847 B2
(45) Date of Patent: Jun. 30, 2026

(54) SYSTEM AND METHOD FOR COMBATING INFECTIONS DUE TO PATHOGENS BELONGING TO PHYLUM PROTEOBACTERIA

(71) Applicant: Tata Consultancy Services Limited, Mumbai (IN)

(72) Inventors: Sharmila Shekhar Mande, Pune (IN); Swadha Anand, Pune (IN); Preethi Alagarai Sampath, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 1219 days.

(21) Appl. No.: 17/596,197

(22) PCT Filed: Jun. 4, 2020

(86) PCT No.: PCT/IB2020/055268
§ 371 (c)(1),
(2) Date: Dec. 3, 2021

(87) PCT Pub. No.: WO2020/245758
PCT Pub. Date: Dec. 10, 2020

(65) Prior Publication Data
US 2022/0389484 A1 Dec. 8, 2022

(30) Foreign Application Priority Data
Jun. 6, 2019 (IN) .............................. 201921022520

(51) Int. Cl.
| | |
|---|---|
| *C12Q 1/689* | (2018.01) |
| *C12N 9/22* | (2006.01) |
| *C12N 15/10* | (2006.01) |
| *C12N 15/11* | (2006.01) |
| *C12N 15/113* | (2010.01) |
| *C12N 15/63* | (2006.01) |

(52) U.S. Cl.
CPC .............. *C12Q 1/689* (2013.01); *C12N 9/22* (2013.01); *C12N 15/102* (2013.01); *C12N 15/111* (2013.01); *C12N 15/113* (2013.01); *C12N 15/63* (2013.01); *C12N 2310/20* (2017.05)

(58) Field of Classification Search
CPC ........ C12Q 1/689; C12N 9/22; C12N 15/102; C12N 15/111; C12N 15/113; C12N 15/63; Y02A 50/30
See application file for complete search history.

(56) References Cited

U.S. PATENT DOCUMENTS

| | | | |
|---|---|---|---|
| 9,028,841 B2 | 5/2015 | Henn et al. | |
| 9,084,423 B2 | 7/2015 | Melander et al. | |
| 10,251,914 B2 | 4/2019 | Sadowsky et al. | |
| 2014/0315985 A1 | 10/2014 | May et al. | |
| 2018/0340218 A1* | 11/2018 | Abudayyeh .......... C12Q 1/6869 |

FOREIGN PATENT DOCUMENTS

WO WO-2011156795 A2 * 12/2011 ........... C12Q 1/6853

OTHER PUBLICATIONS

Tobes, R. and Pareja, E, BMC Genomics, vol. 7, Issue 62, Mar. 24, 2006. (Year: 2006).*
Dworkin M, et al. The Prokaryotes, 3rd Edition, vol. 5, Singapore, Springer Science+Business Media, 2006 (Year: 2006).*
Belkum, A. et. al., Microbiology and Molecular Biology Reviews, vol. 62, No. 2, p. 275-293, Jun. 1998 (Year: 1998).*
Dark, M., Infection and Drug Resistance, 2013:6, p. 115-123, Oct. 7, 2013 (Year: 2013).*
Farhadi, S. et. al., Bioconjugate Chemistry, vol. 29, p. 649-656, Dec. 29, 2017 (Year: 2017).*
Tobes, Raquel, et al., "Bacterial repetitive extragenic palindromic sequences are DNA targets for Insertion Sequence elements", Title of the item: Research article, Date: Mar. 2006, Publisher: BMC Genomics, https://bmcgenomics.biomedcentral.com/track/pdf/10.1186/1471-2164-7-62.pdf.
International Search Report and Written Opinion mailed Aug. 13, 2021, in International Application No. PCT/IB2020/055268; 9 pages.
GenBank Accession No. AP019700, Stella humosa ATCC 43930 DNA, complete genome, Jun. 4, 2019 [online]. (Retrieved on Jun. 30, 2021]. Retrieved from the internet: <URL: https://www.ncbi.nlm.nih.gov/nuccore/AP019700>.
GenBank Accession No. CP033071, *Streptomyces albus* strain ZD11 chromosome, complete genome, Oct. 23, 2018 (online]. [Retrieved on Jun. 30, 2021]. Retrieved from the internet: <URL: https://www.ncbi.nlm.nih.gov/nuccore/CP033071 >.
(Continued)

*Primary Examiner* — Neil P Hammell
*Assistant Examiner* — Krishna N Ravindra
(74) *Attorney, Agent, or Firm* — Finnegan, Henderson, Farabow, Garrett & Dunner, LLP

(57) ABSTRACT

Many of the known infectious pathogens that pose a challenge to available treatment methods because of their antibiotic resistant properties, belong to the phylum Proteobacteria. A method and system for combating infections due to pathogens belonging to phylum Proteobacteria is provided. The system is configured to provide strategies to combat pathogenic infections caused by multi-drug resistant (MDR) and extensively drug resistant (XDR) strains of pathogens belonging to phylum Proteobacteria. It is possible to target multiple pathogens simultaneously using a single target site as these pathogens belong to the same phylum and share similarities in their genetic signature. The strategy involves identifying potential target sites in the pathogen, which can be utilized to compromise its multiple virulence or essential functions at the same time.

19 Claims, 8 Drawing Sheets

Specification includes a Sequence Listing.

(56)           References Cited

OTHER PUBLICATIONS

GenBank Accession No. CP026244, Scophthalmus maximus chromosome 2, Jun. 5, 2018 [online]. [Retrieved on Jun. 30, 2021]. Retrieved from the internet: <URL: https://www.ncbi.nlm.nih.gov/nuccore/CP026244>.

GenBank Accession No. AL080312, Human DNA sequence from clone RP5-1025A 1 on chromosome 20p11.21-11.23, complete sequence, Dec. 13, 2012 [online]. [Retrieved on Jun. 30, 2021]. Retrieved from the internet: <URL: https://www.ncbi.nlm.nih.gov/nuccore/AL080312>.

* cited by examiner

*Klebsiella pneumoniae* genome

Legend:

— R-KLEB

— Virulent / essential genes

FIG. 2

Construct used to
target a single pathogen
using single probe

Construct used to
target multiple
pathogens
using single probe

| | | |
|---|---|---|
| ■ | – | R-ELEMENT |
| (dotted) | – | ENZYME 1 |
| (hatched) | – | ENZYME 2 |

| | | |
|---|---|---|
| ■ | – | R-ELEMENT<br>Present in more than<br>one pathogen |
| (dotted) | – | ENZYME 1 |
| (hatched) | – | ENZYME 2 | nick

*Yersinia pestis* genome

Enzymatic cleavage in either directions

— Virulent gene

— R-YER

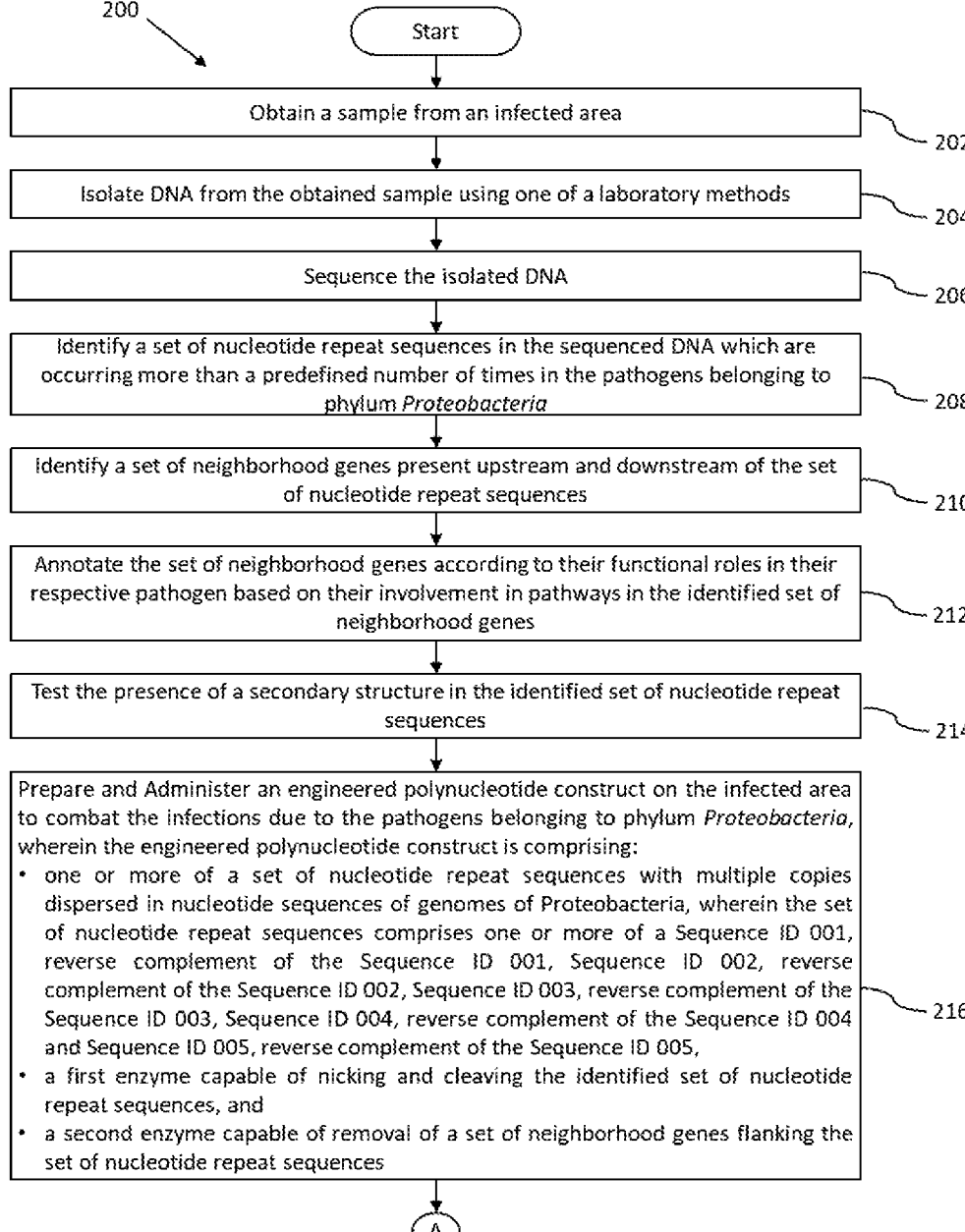

200

Start

Obtain a sample from an infected area
202

Isolate DNA from the obtained sample using one of a laboratory methods
204

Sequence the isolated DNA
206

Identify a set of nucleotide repeat sequences in the sequenced DNA which are occurring more than a predefined number of times in the pathogens belonging to phylum *Proteobacteria*
208

Identify a set of neighborhood genes present upstream and downstream of the set of nucleotide repeat sequences
210

Annotate the set of neighborhood genes according to their functional roles in their respective pathogen based on their involvement in pathways in the identified set of neighborhood genes
212

Test the presence of a secondary structure in the identified set of nucleotide repeat sequences
214

Prepare and Administer an engineered polynucleotide construct on the infected area to combat the infections due to the pathogens belonging to phylum *Proteobacteria*, wherein the engineered polynucleotide construct is comprising:
• one or more of a set of nucleotide repeat sequences with multiple copies dispersed in nucleotide sequences of genomes of Proteobacteria, wherein the set of nucleotide repeat sequences comprises one or more of a Sequence ID 001, reverse complement of the Sequence ID 001, Sequence ID 002, reverse complement of the Sequence ID 002, Sequence ID 003, reverse complement of the Sequence ID 003, Sequence ID 004, reverse complement of the Sequence ID 004 and Sequence ID 005, reverse complement of the Sequence ID 005,
• a first enzyme capable of nicking and cleaving the identified set of nucleotide repeat sequences, and
• a second enzyme capable of removal of a set of neighborhood genes flanking the set of nucleotide repeat sequences
216

SEQUENCE LISTING

```
<160> NUMBER OF SEQ ID NOS: 5

<210> SEQ ID NO 1
<211> LENGTH: 28
<212> TYPE: DNA
<213> ORGANISM: Salmonella enterica
<220> FEATURE:
<221> NAME/KEY: misc_feature
<222> LOCATION: (14)..(15)
<223> OTHER INFORMATION: n is a, c, g, or t
<220> FEATURE:
```

-continued

```
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 1
ssctgatrry rctnngcntn tcnggcct                                              28

<210> SEQ ID NO 2
<211> LENGTH: 34
<212> TYPE: DNA
<213> ORGANISM: Klebsiella pneumoniae
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: Optional_nucleotides
<222> LOCATION: (15)..(24)
<223> OTHER INFORMATION: These nucleotides may be present or absent in
     the sequence
<220> FEATURE:
<221> NAME/KEY: misc_feature
<222> LOCATION: (15)..(24)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 2
ggccgggnnn ggcgnnnnnn nnnncgccnc ccgg                                       34

<210> SEQ ID NO 3
<211> LENGTH: 24
<212> TYPE: DNA
<213> ORGANISM: Neisseria gonorrhoeae
<220> FEATURE:
<221> NAME/KEY: Optional_nucleotides
<222> LOCATION: (9)..(14)
<223> OTHER INFORMATION: The nucleotides may be absent or present in the
     sequence
<220> FEATURE:
<221> NAME/KEY: misc_feature
<222> LOCATION: (9)..(14)
<223> OTHER INFORMATION: n is a, c, g, or t

<400> SEQUENCE: 3
rycgtctgnn nnnnttcaga yrrc                                                  24

<210> SEQ ID NO 4
<211> LENGTH: 24
<212> TYPE: DNA
<213> ORGANISM: Neisseria meningitidis
<220> FEATURE:
<221> NAME/KEY: Optional_nucleotides
<222> LOCATION: (9)..(14)
<223> OTHER INFORMATION: The nucleotides may be absent or present in the
     sequence
<220> FEATURE:
<221> NAME/KEY: misc_feature
<222> LOCATION: (9)..(14)
<223> OTHER INFORMATION: n is a, c, g, or t

<400> SEQUENCE: 4
```

-continued

```
rycgtctgnn nnnnttcaga yrrc                                             24

<210> SEQ ID NO 5
<211> LENGTH: 22
<212> TYPE: DNA
<213> ORGANISM: Yersinia pestis
<220> FEATURE:
<221> NAME/KEY: Optional_nucleotides
<222> LOCATION: (13)..(19)
<223> OTHER INFORMATION: The nucleotides may be present or absent in the
      sequence
<220> FEATURE:
<221> NAME/KEY: misc_feature
<222> LOCATION: (13)..(19)
<223> OTHER INFORMATION: n is a, c, g, or t

<400> SEQUENCE: 5
gcygcyttcc ygnnnnnnng mr                                               22
```

SYSTEM AND METHOD FOR COMBATING INFECTIONS DUE TO PATHOGENS BELONGING TO PHYLUM PROTEOBACTERIA

PRIORITY CLAIM

This application is a U.S. National Stage Filing under 35 U.S.C. § 371 and claims priority from International Application No. PCT/IB2020/055268, filed on Jun. 4, 2020, which application claims priority under 35 U.S.C. § 119 from India application No. 201921022520, filed on Jun. 6, 2019. The entire contents of the aforementioned application are incorporated herein by reference.

REFERENCE TO SEQUENCE LISTING SUBMITTED ELECTRONICALLY

An official copy of the sequence listing is submitted electronically via EFS-WEB as an ASCII formatted sequence listing with a file named Proteo_ST25, created on Nov. 3, 2025, having a size of 2,388 bytes. The sequence listing contained in this ASCII formatted document is part of the specification and is herein incorporated by reference in its entirety.

TECHNICAL FIELD

The embodiments herein generally relate to the field of Proteobacteria infections, and, more particularly, to a method and system for combating the problem of multidrug resistance resulting due to infection of pathogens belonging to phylum Proteobacteria.

BACKGROUND

Many of the known infectious pathogens that pose a challenge to available treatment methods because of their antibiotic resistant properties belong to the phylum Proteobacteria. Some of the common but prevalent diseases include typhoid caused by *Salmonella*, pneumonia caused by *Klebsiella* and gonorrhoea caused by *Neisseria* gonorrhoea to name a few. All the above mentioned pathogens belong to phylum Proteobacteria and have been known to be notoriously difficult to treat because of rapidly spreading antimicrobial resistance amongst them. In fact, it has been observed that the antimicrobial resistance in *Yersinia pestis* that causes plague was obtained through horizontal gene transfer from *E. coli*, another member of Proteobacteria phylum.

CDC (Centre for Disease Control and Prevention) has classified *Neisseria* gonorrhoea as category urgent threat as the resistance has been observed in the last class of antibiotics (ceftriaxone) used in its treatment. Similarly, rapid carbapenem resistance is globally spreading in *Klebsiella pneumonia* making it challenging to treat pneumonia infections caused by this pathogen.

Various methods have been used in the prior art for treating infections caused by the pathogens from the Proteobacteria phylum. Antibiotics are the most common method of treating these pathogens. The most commonly used antibiotics are nalidixic acid, carbapenem, Cefprozil, Cefuroxim, doxycyclin, furazolidone, ceftriaxone, cefixime etc. Studies have shown that these pathogens are rapidly developing resistance to these antibiotics. The antibiotic resistance genes are further transferred from one bacterium to another utilizing several transfer methods. Additional problems arise which pertain to formation of biofilms in these bacteria which allows them to evade antibiotics. Several studies have shown that biofilm formation inhibitors (like several enzymes which degrade the matrix) as well as quorum quenchers (prevent biofilm formation) can prove useful in this regard. Despite utilizing these inhibitors several bacteria still escape the antibiotics and lead to relapse once the treatment is stopped. Several side effects and cross reactivity is observed in present drugs. Most of the antibiotics land up killing the beneficial human microbiome also.

Another approach involves utilizing mechanisms to elicit an immune response in host against several antigenic/virulent proteins. Antisense oligomers based silencing mechanism are also often used to impede functioning of certain genes in pathogens.

SUMMARY

Embodiments of the present disclosure present technological improvements as solutions to one or more of the above-mentioned technical problems recognized by the inventors in conventional systems. For example, in one embodiment the system for combating infections due to pathogens belonging to phylum Proteobacteria is provided. The system comprises a sample collection module, a pathogen detection and DNA extraction module, a sequencer, one or more hardware processors, a memory, an administration module and an efficacy module. The sample collection module obtains a sample from an infected area. The pathogen detection and DNA extraction module isolates DNA from the obtained sample using one of laboratory methods. The sequencer sequences the isolated DNA. The memory in communication with the one or more hardware processors, wherein the one or more first hardware processors are configured to execute programmed instructions stored in the one or more first memories, to: identify a set of nucleotide repeat sequences in the sequenced DNA which are occurring more than a predefined number of times in the pathogens belonging to phylum Proteobacteria; identify a set of neighborhood genes present upstream and downstream of the set of nucleotide repeat sequences; annotate the set of neighborhood genes according to their functional roles in their respective pathogen based on their involvement in pathways in the identified set of neighborhood genes; test the presence of a secondary structure in the identified set of nucleotide repeat sequences. The administration module prepares and administers an engineered polynucleotide construct on the infected area to combat the infections due to the pathogens belonging to phylum Proteobacteria, wherein the engineered polynucleotide construct is comprising: one or more of a set of nucleotide repeat sequences with multiple copies dispersed in nucleotide sequences of genomes of Proteobacteria, wherein the set of nucleotide repeat sequences comprises one or more of a Sequence ID 001, reverse complement of the Sequence ID 001, Sequence ID 002, reverse complement of the Sequence ID 002, Sequence ID 003, reverse complement of the Sequence ID 003, Sequence ID 004, reverse complement of the Sequence ID 004 and Sequence ID 005, reverse complement of the Sequence ID 005, a first enzyme capable of nicking and cleaving the identified set of nucleotide repeat sequences, and a second enzyme capable of removal of a set of neighborhood genes flanking the set of nucleotide repeat sequences. The efficacy module checks the efficacy of the administered engineered polynucleotide construct to combat the pathogens belonging to phylum Proteobacteria after a predefined time period; and re-administer the engineered polynucleotide construct if the pathogens belonging to phylum Proteobacteria are still present in the infected area post administering.

In another aspect, a method for combating infections due to pathogens belonging to phylum Proteobacteria is provided. Initially, a sample is obtained from an infected area. Later DNA is isolated and extracted DNA from the obtained sample using one of a laboratory methods. Further, the isolated DNA is sequenced. In the next step, a set of nucleotide repeat sequences is identified in the sequenced DNA which are occurring more than a predefined number of times in the pathogens belonging to phylum Proteobacteria. Later, a set of neighborhood genes is identified present upstream and downstream of the set of nucleotide repeat sequences. Further, the set of neighborhood genes is annotated according to their functional roles in their respective pathogen based on their involvement in pathways in the identified set of neighborhood genes. The presence of a secondary structure is then tested in the identified set of nucleotide repeat sequences. In the next step, an engineered polynucleotide construct is prepared and administered on the infected area to combat the infections due to the pathogens belonging to phylum Proteobacteria, wherein the engineered polynucleotide construct is comprising: one or more of a set of nucleotide repeat sequences with multiple copies dispersed in nucleotide sequences of genomes of Proteobacteria, wherein the set of nucleotide repeat sequences comprises one or more of a Sequence ID 001, reverse complement of the Sequence ID 001, Sequence ID 002, reverse complement of the Sequence ID 002, Sequence ID 003, reverse complement of the Sequence ID 003, Sequence ID 004, reverse complement of the Sequence ID 004 and Sequence ID 005, reverse complement of the Sequence ID 005, a first enzyme capable of nicking and cleaving the identified set of nucleotide repeat sequences, and a second enzyme capable of removal of a set of neighborhood genes flanking the set of nucleotide repeat sequences. Later, the efficacy of the administered engineered polynucleotide construct is checked to combat the pathogens belonging to phylum Proteobacteria after a predefined time period. And finally, the engineered polynucleotide construct is re-administered if the pathogens belonging to phylum Proteobacteria are still present in the infected area post administering.

In an aspect, the target sites or nucleotide repeat sequences in this disclosure refer to nucleotide sequences which repeat a minimum number of ten times within the genome of the candidate pathogen/pathogens which are identified in an infected site from which the sample is collected. These nucleotide repeat sequences can be targeted in order to debilitate the pathogens belonging to phylum Proteobacteria. The mentioned nucleotide repeat sequence/ sequences is selected if it occurs more than 10 times in all the pathogenic strains of the candidate specie or genus to which the candidate pathogen/pathogens identified in an infected site belong. The nucleotide repeat sequence is selected such that it does not occur more than twice in genomes of strains belonging to any other genus than that of the candidate pathogen and does not occur more than twice within the genome of the host.

In yet another aspect, one or more non-transitory machine readable information storage mediums comprising one or more instructions which when executed by one or more hardware processors cause combating infections due to pathogens belonging to phylum Proteobacteria. Initially, a sample is obtained from an infected area. Later DNA is isolated and extracted DNA from the obtained sample using one of a laboratory methods. Further, the isolated DNA is sequenced. In the next step, a set of nucleotide repeat sequences is identified in the sequenced DNA which are occurring more than a predefined number of times in the pathogens belonging to phylum Proteobacteria. Later, a set of neighborhood genes is identified present upstream and downstream of the set of nucleotide repeat sequences. Further, the set of neighborhood genes is annotated according to their functional roles in their respective pathogen based on their involvement in pathways in the identified set of neighborhood genes. The presence of a secondary structure is then tested in the identified set of nucleotide repeat sequences. In the next step, an engineered polynucleotide construct is prepared and administered on the infected area to combat the infections due to the pathogens belonging to phylum Proteobacteria, wherein the engineered polynucleotide construct is comprising: one or more of a set of nucleotide repeat sequences with multiple copies dispersed in nucleotide sequences of genomes of Proteobacteria, wherein the set of nucleotide repeat sequences comprises one or more of a Sequence ID 001, reverse complement of the Sequence ID 001, Sequence ID 002, reverse complement of the Sequence ID 002, Sequence ID 003, reverse complement of the Sequence ID 003, Sequence ID 004, reverse complement of the Sequence ID 004 and Sequence ID 005, reverse complement of the Sequence ID 005, a first enzyme capable of nicking and cleaving the identified set of nucleotide repeat sequences, and a second enzyme capable of removal of a set of neighborhood genes flanking the set of nucleotide repeat sequences. Later, the efficacy of the administered engineered polynucleotide construct is checked to combat the pathogens belonging to phylum Proteobacteria after a predefined time period. And finally, the engineered polynucleotide construct is re-administered if the pathogens belonging to phylum Proteobacteria are still present in the infected area post administering.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

Figure 2:
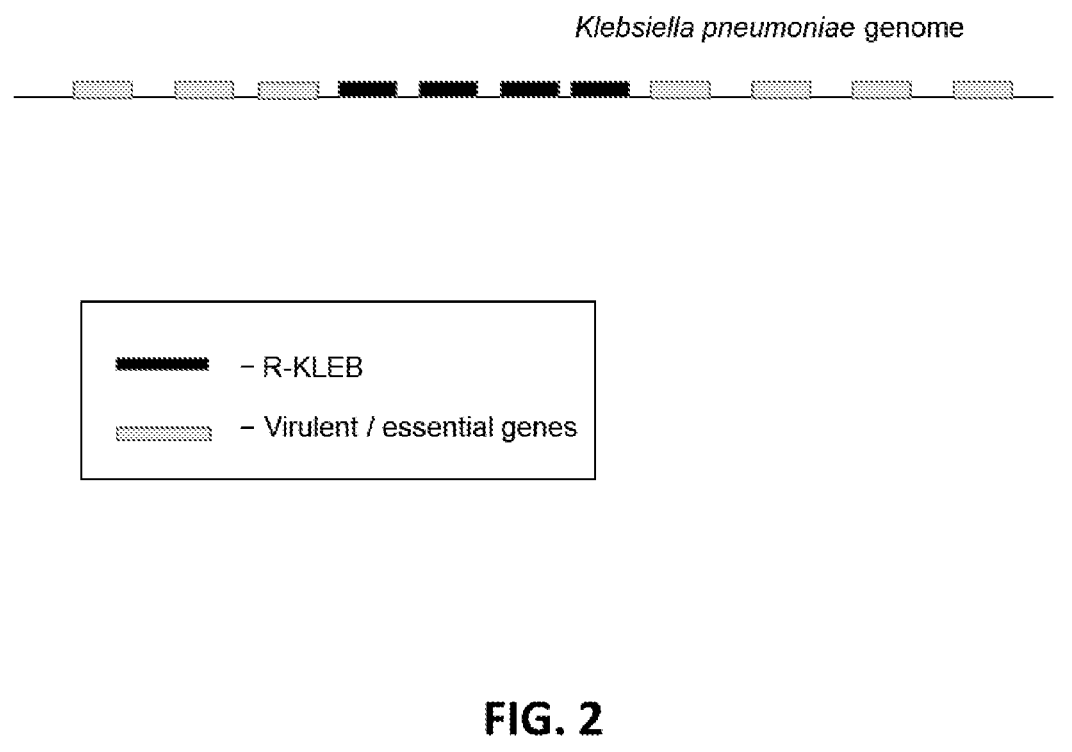

FIG. 2 shows nucleotide repeat sequences along with neighborhood genes in the *Klebsiella pneumoniae* genome as an example according to an embodiment of the disclosure.

FIG. 6A-6B is a flowchart illustrating the steps involved in combating infections due to pathogens belonging to phylum Proteobacteria according to an embodiment of the present disclosure It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Figure 1:
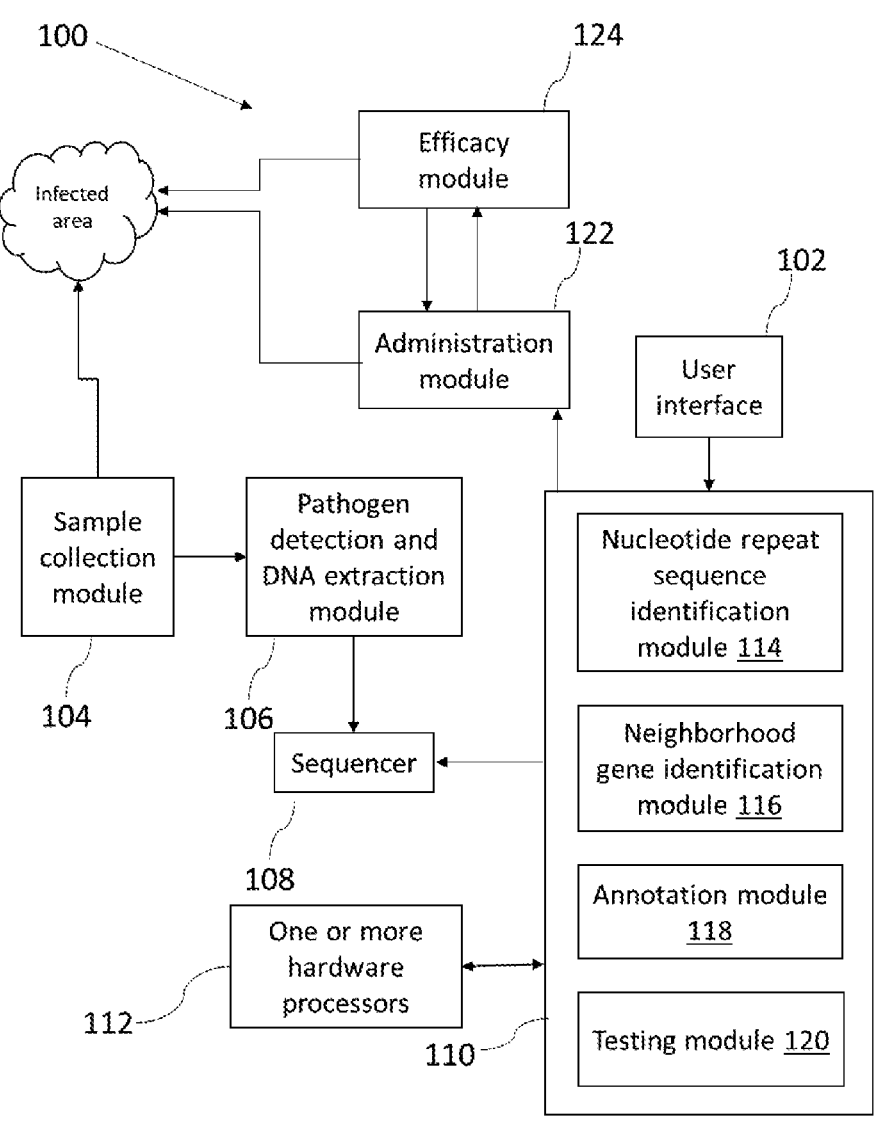
FIG. 1 illustrates a block diagram of a system for combating infections due to pathogens belonging to phylum Proteobacteria according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Glossary—Terms Used in the Embodiments

The expression "nucleotide repeat sequences" or "repeated nucleotide sequences" or "the set of nucleotide repeats" or "repeated sequence regions" or "target sequence" or "target sites" or "similar sequence stretches" or "repeat element" in the context of the present disclosure refers to nucleotide sequences which have been repeated multiple times in a sequence of DNA extracted from a sample obtained from the infected area or within nucleotide sequence obtained for a genome of a pathogen.

The term "metagenome" refers to the genetic material derived directly from the infected site and can be considered representative of overall microorganisms present in a sample collected from an environment. The information about metagenome and its taxonomic constitution is obtained by either sequencing the genes considered as markers for different taxa (For example 16S rRNA), amplifying genes of interest using specific primers through methods like but not limited to Polymerase Chain Reaction (PCR). This information can also be obtained by whole genome sequencing of the obtained environmental or metagenomic sample. The sample collected from the environment is referred to from now on as metagenomic sample.

The term "identified nucleotide repeat sequence is dispersed across distant locations in the pathogen genome" refers to the fact that the nucleotide sequences identified in this method are spread at distant locations across the pathogen genome and is not clustered together at one particular location alone on the genome.

In this disclosure, the terms "distant location" or "distinct location" or "dispersed sequences" refer to locations of two repeat sequences that are separated by >10000 base pairs. Nucleotide repeat regions having distance less than 10000 base pairs between their locations have been considered as clustered repeats.

The expression "candidate genus" or "candidate pathogen" refers to the genus, species or pathogen in which the nucleotide repeat sequence is identified and is used as a target sequence/site.

The term "commensal" refers to microbes which are considered beneficial to the host or cause no harm to the host.

The term 'pathogen' refers to microbe/microbes which cause a disease in host.

The term 'host' refers to either a living organism or an environmental site. In an embodiment, 'host' may refer to human, animal or plant in which a pathogenic infection may be observed.

The term 'non-culturable' refers to microbes that cannot be grown in a laboratory settings because the ideal conditions and media for their growth is not well characterized. Such microbes can be analyzed by culture independent methods discussed in various embodiments of the disclosure.

Majority of the existing methods for combating pathogens focus on silencing specific genes in order to curtail their expression. Targeting single functional aspects of bacteria often is not sufficient as bacteria might mutate the targets and develop resistance to the therapeutic intervention. To overcome the drawbacks of the existing methods, the present system and method deals with identifying and targeting multiple copies of a nucleotide repeat sequence at distant locations on the genome as well as the important functional genes flanking this sequence. Therefore, the method allows to debilitate multiple important functions of the pathogen simultaneously The important functional genes in this disclosure refer to the genes in pathogens which encode for proteins which are critical for survival, pathogenicity, interaction with the host, adherence to the host or for the virulence of bacteria. Development of resistance in pathogens to the method mentioned in this disclosure is difficult as the pathogen will have to bring about multiple mutations in distant locations. The present disclosure includes targeting multiple virulence and essential proteins of pathogens. The method may also include targeting various other proteins performing important functions (metabolism, host interactions, pathogenicity etc.) in bacteria.

Referring now to the drawings, and more particularly to FIG. 1 through FIG. 6B, where similar reference characters denote corresponding features consistently throughout the figures, there are shown preferred embodiments and these embodiments are described in the context of the following exemplary system and/or method.

According to an embodiment of the disclosure, a system 100 for combating infections due to pathogens belonging to phylum Proteobacteria is shown in the block diagram of FIG. 1. The system 100 is configured to provide strategies to combat pathogenic infections caused by multi-drug resistant (MDR) and extensively drug resistant (XDR) strains of pathogens belonging to phylum Proteobacteria. It is possible to target multiple pathogens simultaneously using a single target site as these pathogens belong to the same phylum and share similarities in their genetic signature.

The strategy involves identifying potential target sites in a pathogen, which can be utilized to compromise its multiple virulence or essential functions at the same time. The idea used in this disclosure utilizes the fact that a conserved stretch of nucleotide sequence occurring multiple times on a pathogen genome in genomic neighbourhood of genes encoding virulence factors or in vicinity of genes essential for pathogen survival encoded within the genome of the candidate pathogen can be targeted to disrupt the overall genetic machinery of the pathogens belonging to phylum Proteobacteria. These nucleotide repeat sequences might also lie in the neighborhood of genes which perform other critical functions in a pathogen.

In the present disclosure genomic neighbourhood or vicinity or 'flanking genes' refers to regions lying within a predefined number of genes to the selected nucleotide repeat sequence (or its reverse complement) on the nucleotide sequence of the candidate pathogen genome or within a distance of predefined number of bases with respect to the selected nucleotide repeat sequence (or its reverse complement) on the nucleotide sequence of the pathogen genome. The flanking genes are found on each strand on pathogen genomic DNA. In an embodiment the genomic neighbourhood or flanking genes may comprise of 10 genes lying on either side of nucleotide repeat sequence or its reverse complement in terms of its location on the pathogen genome. The reverse complement of target sequence is obtained by interchanging letters A and T and interchanging letters C and G between target and complement sequence. The reverse complement refers to the sequence corresponding to the identified nucleotide repeat sequence in the opposite strand of DNA.

A conserved stretch of sequence refers to a nucleotide repeat sequence which occurs A conserved stretch of sequence refers to a nucleotide repeat sequence which occurs within all pathogenic genomes belonging to a candidate genus. Another important factor would be occurrence of these sequences only in the genomic sequence of multiple pathogenic strains of candidate pathogen and minimum cross reactivity with the commensals (belonging to same candidate genus or other genera) as well as the host. Cross reactivity, in this disclosure, refers to the occurrence of these conserved stretches of nucleotide sequences more than twice in the host genome or more than twice in genera other than the candidate genus or more than twice within commensal bacteria belonging to the candidate genus for which this sequence is being utilized as a target. Further, the identified potential target sites in pathogen are not specific to a single strain of the pathogen. In most cases, metagenomic samples contain bacteria whose strain level information cannot be obtained. Thus, the method can be utilized to target all strains of pathogens in the given candidate genus/species of the bacteria and is not hindered by the absence of strain level information.

According to an embodiment of the disclosure, the system 100 consists of a user interface 102, a sample collection module 104, a DNA extraction module 106, a sequencer 108, a memory 110 and one or more hardware processors 112 as shown in FIG. 1. The one or more hardware processors 112 is in communication with the memory 110. The memory 110 further includes a plurality of modules for performing various functions. The memory 110 may include a nucleotide repeat sequence identification module 114, a neighborhood gene identification module 116, an annotation module 118 and a testing module 120. The system 100 further comprises an administration module 122 and an efficacy module 124 as shown in the block diagram of FIG. 1.

According to an embodiment of the disclosure, the sample is collected from the infected area using the sample collection module 104. In this module, the method utilized for extracting samples from the infected sites depends largely on the site of infection. In an embodiment, in cases of topical infection in a living organism (for e.g., skin infections caused during advance stages of *Neisseria gonorrhoeae* infection etc.), the sample may be collected from the infected sites such as skin, mucosal lining of tissues such as eyes, mouth and vagina. Various techniques are used as per the guidance of the physician such as a sterile swab (for example cotton swabs) for sample collection from the mucosal lining and saliva, a sterile syringe for sample collection from the pus and aspirations of fluids. A skin scrape can also be performed for sample collection from the infected sites on the skin. Also tissue biopsy can be performed in order to obtain the samples.

In an embodiment where the site of infection is an internal organ such as lung, gut etc., different techniques are employed based on the organ from which the sample is being collected. In one embodiment, where the infection is in lung (for example infection caused by *Klebsiella pneumoniae*), sample collection from the fluids in the lung due to the infection could be done by one of the following methods such as bronchoalveolar lavage collection, bronchial brushings, endobronchial biopsies and nasal scrape etc. In an embodiment, in case of infection in the upper respiratory tract sample collection from lung can be performed by oropharyngeal (OP) and nasopharyngeal (NP) swabs and sputum collection. In yet another embodiment where site of infection is the gut (for example infection caused by *Salmonella* sp.), fecal samples may be collected to identify the pathogen infecting the gut. Samples may be collected using Endoscopic biopsy of gastrointestinal tract in cases where the infection does not present in the fecal sample.

In an embodiment, in case of blood borne pathogens such as *Yersinia pestis*, the sample may be extracted through collection of blood components. Acute serum collected from the patients (containing high concentration of infectious bacteria) can be used. Additionally, the whole blood sample can be submitted for bacterial culturing or the whole blood plasma can be utilized for further procedure.

In an embodiment, the site of infection can also be an environment such as soil, air, water or surfaces etc. Sample collection from a surface can be performed through the use of sterile swab. Dry swabs may be recommended for wet surfaces and wet swabs may be recommended for dry surfaces. Swabbing of the test surface maybe performed by rolling the swab lightly back and forth. Water and soil samples may be collected from the environmental site of infection and sent for further procedure. Air samples can also be collected to identify the presence of air borne pathogen. Volumetric air samples for culture analyses can be taken by impacting a known volume of air onto a suitable growth medium. Any other laboratory accepted method of sample extraction/collection from environment as well as living organisms is within the scope of this invention.

It should be appreciated, that the bacterial cells are isolated from the extracted sample before being presented to pathogen detection and DNA extraction module 106 in cases where the pathogen is known to be culturable. In case of non-culturable pathogen, the collected samples are directly processed to pathogen detection and DNA extraction module 106. DNA is isolated and then extracted from the sample using laboratory standardized protocol using the pathogen detection and DNA extraction module 106 and sequencing is performed using the sequencer 108. It should be appreciated, that the bacterial cells are isolated from the extracted sample before being presented to pathogen detection and DNA extraction module 106 in cases where the pathogen is known to be culturable. In case of non-culturable pathogen, the collected samples are directly processed to pathogen detection and DNA extraction module 106, DNA/RNA is isolated and extracted from the sample using laboratory standardized protocols using the pathogen detection and DNA extraction module 106 and sequencing is performed using the sequencer 108. The nucleotide sequences obtained after sequencing of extracted DNA/RNA sequences are then provided to the processor 112 using the user interface 102. The nucleotide sequences can be obtained for 16S rRNA, a nucleotide sequence encoding for any particular protein of interest being amplified, or sequences corresponding to DNA fragments for whole genome sequencing or shotgun sequencing. In one embodiment, DNA/RNA can be extracted using miniprep isolation kits and other methods standardized in laboratory setups. The extracted DNA is then provided into the sequencer 108 and the sequences so obtained are fed into the processor 112 using the user interface 102. The user interface 102 is operated by a user. The user interface 102 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

The pathogen detection and DNA extraction module 106 is also configured to utilize experimental techniques to detect pathogens present in an infected site. The use of any laboratory acceptable methods of detecting presence of pathogens present at the infected site is within scope of the disclosure. In one embodiment, presence of viable living cells can be detected by utilizing presence of bacterial mRNA which has a short half-life and will not exist once the cells are dead. This mRNA based method may involve identifying antigen/protein specific for the pathogen which can be utilized as a marker for that pathogen and produced by the pathogen in abundance and the corresponding gene on the pathogen genome can be obtained (For e.g. Caf1 gene in *Yersinia*, invA in *Salmonella* and cppB in *Neisseria gonorrhoeae* etc.). The mRNA corresponding to expression of these genes can be detected using techniques like but not limited to polymerase chain reaction (RT-PCR) assays or reverse transcriptase strand displacement amplification (RT-SDA) assays. In another embodiment, expression of proteins identified as specific to these pathogens can be detected using various laboratory accepted methods for protein purification and detection (For e.g. Caf1 gene in *Yersinia*, invA in *Salmonella* and cppB in *Neisseria gonorrhoeae* etc.). Chromogenic enzyme assays for a pathogen are also within scope of the invention. Specific metabolites (sugar metabolism in *Neisseria gonorrhoeae* by rapid non-growth tests) or compounds produced by a pathogen can also be detected (using different laboratory acceptable methods like Mass spectrometry, HPLC-MS, spectrometry-based methods etc.) to ascertain pathogen presence. In other embodiments, the identified antigens (Caf1 gene in *Yersinia pestis*, invA in *Salmonella* and cppB in *Neisseria gonorrhoeae*)/marker sequences can be targeted using methods like nucleic acid amplification tests (NAAT), real time PCR, immunoassays (For e.g. antibodies against Proteins IA and IB in *Neisseria gonorrhoeae*) etc. as well as specific staining and microscopy techniques and flow cytometry methods of detecting pathogens are also within scope of this invention. PCR or Restriction Fragment Length Polymorphism (RFLP) based detection of 16S rRNA in order to identify pathogens can also be utilized (For e.g. Pace 2NG for detection of *Neisseria gonorrhoeae*). In one more embodiment, staining methods can also be utilized to identify a pathogen and establish viability of a pathogen cell (e.g. propidium iodide can be used for identifying dead cells). Cell toxicity assays can also be utilized for toxins based detection of pathogens. Further in case of sporulating bacteria, spore detection assays can also be utilized. In case of culturable bacteria, the viability of pathogens can even be established using culturing methods using selective media followed by methods to detect specific pathogens discussed above. In case of an infection in living beings observation of phenotypic effects like alleviation of infection symptoms is also within scope of this disclosure. The symptoms may vary with type of infection and may be observed by registered medical practitioner or healthcare professional. Any other method of detecting pathogens are also within scope of this disclosure.

According to an embodiment of the disclosure, the DNA extraction module 106 is configured to applying one or more techniques for identification or detection of microbes in a collected sample comprising a sequencing technique, a flow cytometry based methodology, a microscopic examination of the microbes in collected sample, microbial culture of pathogens in vitro, immunoassays, cell toxicity assay, enzymatic, colorimetric or fluorescence assays, assays involving spectroscopic/spectrometric/chromatographic identification and screening of signals from complex microbial populations, The pathogen or microbial characterization data may comprise one or more of sequenced microbial DNA data, a Microscopic imaging data, a Flow cytometry cellular measurement data, a colony count and cellular phenotypic data of microbes grown in in-vitro cultures, immunological data, proteomic/metabolomics data, and a signal intensity data. The sequenced microbial data obtained from sequencer may comprise of one or more of sequences obtained from next generation sequencing platforms comprising marker genes including 16S rRNA, Whole Genome Shotgun (WGS) sequencing, a fragment library based sequencing technique, a mate-pair library or a paired-end library based sequencing technique, or a combination thereof. The sequencing data may also comprise of complete genome sequences of the pathogens obtained within a collected sample. In one embodiment, the taxonomic groups or pathogens within a sample collected can be obtained by amplification of marker genes like 16S rRNA within bacteria. In another embodiment, the taxonomic groups or pathogens within a sample can be obtained by the binning of whole genome sequencing reads into various taxonomic groups using different methods including sequence similarities as well as several methods using supervised and unsupervised classifiers for taxonomic binning of metagenomics sequences.

According to an embodiment of the disclosure, the processor 112 comprises the nucleotide repeat sequence identification module 114. The nucleotide repeat sequence identification module 114 is configured to identify a set of nucleotide repeat sequences in the extracted DNA which occur more than a predefined number of times (refers to the number of occurrences of nucleotide repeat sequence on a genome in a dispersed manner and this number might vary with system and pathogen under consideration) in the genomes of the pathogens belonging to phylum Proteobacteria and are dispersed at distant locations on the genome. The predefined number refers to the number of occurrences of nucleotide repeat sequence on a genome of the genomic sequences of all pathogenic strains of candidate pathogen in a dispersed manner and this number might vary with system and pathogen under consideration. A minimum of 10 occurrences is required for a nucleotide repeat sequence to be considered. The nucleotide repeat elements/sequences in the genomes of the pathogens belonging to phylum Proteobacteria may be collectively referred as R-PROTEO. In an example, R-KLEB is identified as one example of nucleotide repeat element/sequences corresponding to *Klebsiella pneumoniae* belonging to phylum Proteobacteria as shown in schematic representation of FIG. 2. Further, it is important to ensure that the identified nucleotide repeat sequence region is specific to a particular candidate pathogenic genus only and on nucleotide based sequence alignment shows no more than two cross matches with commensals of the other genera or commensals within phylum Proteobacteria. Cross match refers to the occurrence of identified nucleotide repeat sequence region more than two times in a genus which is different from the candidate genus in which the nucleotide repeat sequence has been identified as is to be used as a target site.

In addition to that, the identified set of nucleotide sequences are not specific to a single strain of the pathogen. In most cases, metagenomic samples contain bacteria whose strain level information cannot be obtained. Thus, the method can be utilized to target all pathogens in the given candidate genus/species of the pathogen and is not hindered by the absence of strain level information and thus making it more robust.

Following method can be used for the identification of the repeat sequence region.

Conserved nucleotide repeat elements were identified on pathogen genome by taking sequence stretches of predefined length Rn, picked from the genome sequence of candidate pathogen or different strains of candidate pathogen, keeping the difference in the start position of two consecutive nucleotide sequence stretches $Rn_{i+1}$ and $Rn_i$ as 5 nucleotides. Predefined length Rn refers to the length of a stretch of nucleotide sequence (picked from the complete nucleotide sequence of a bacterial genome) used as a seed input for local sequence alignment tools. This predefined length may differ depending on the pathogen. In the next step, a reference genome based nucleotide sequence alignment tool is applied in order to align the sequence stretch with nucleotide sequences corresponding to genomes of all pathogenic strains belonging to the candidate pathogen, genus or specie. Stretches of nucleotide sequences from a pathogen genome were aligned within the nucleotide sequence of same genome and all genomes of candidate genus or candidate pathogen by local alignment (as implemented in PILER software) to find the location of these elements in all sequenced pathogen genomes. Sequence based search utilizing any other sequence alignment or repeat finding tools are within the scope of this invention. If the number of times Rn matches on the genome is greater than the predefined threshold, the nucleotide sequence stretch is termed as R-PROTEO. If the number of times $R_n$ matches on the genomic sequences of strains of candidate pathogen genome/genomes is greater than the predefined threshold with a minimum value of 10, the sequence stretch is termed as target nucleotide repeat sequence, R-PROTEO in this case. A relaxation of two mismatches was allowed to prevent false positives which could lead to over-prediction of possible targets. Nucleotide repeat sequences occurring more than 20 times at distant locations on the genome were considered. This number of occurrences may vary depending on the system requirements. Although, the number of occurrences of the nucleotide repeat sequence might vary in different pathogens, a minimum of 10 occurrences is required for a nucleotide repeat sequence to be considered as a target sequence The dispersed nucleotide sequences at distant locations on the genome refers to stretches of nucleotide sequences which occur across the genome with a distance of predefined number of base pairs between them In one embodiment used in this disclosure the predefined number refers to a separation of >10000 base pairs between two nucleotide repeat sequences.

According to an embodiment of the disclosure, the processor 112 further includes the neighborhood gene identification module 116. The neighborhood gene identification module 116 is configured to identify a set of neighborhood genes present upstream and downstream of the set of nucleotide repeat sequences in the genomes corresponding to pathogens belonging to phylum Proteobacteria. On each genome G of Genus Ge where R-PROTEO or its reverse complement occurs, flanking genes were found on either side and on each strand of Genome G. In this embodiment, 10 genes were included but the span may vary with each system.

According to an embodiment of the disclosure, the system 100 further includes the annotation module 118. The annotation module 118 categorizes or annotates the set of neighborhood genes based on their functional roles in the pathogen. Functional annotation of these genes which in this embodiment was performed using HMM search but can be performed using other methods like PSSM, BLAST etc. Functional categorization of these genes are on the basis of pathways they are involved in. These dispersed nucleotide repeat sequences RPROTEO at distant locations on the genome can be used as targets which can be further extended to target multiple flanking genes (which includes virulence and survival genes) simultaneously at distant multiple locations and carry out changes like but not limited to gene silencing, gene recombination, gene substitution with a new function etc.

Functional categorization of these genes on the basis of pathways they are involved in was carried out using literature mining. In the present embodiment the nucleotide repeat elements were identified on sequenced genomes of *Klebsiella pneumoniae, Neisseria gonorrhoeae, Neisseria meningitides, Salmonella enterica* and *Yersinia pestis* as explained in detail in the later part of disclosure. The broad categories of the same have been provided in Table 1, Table 2, Table 3 and Table 4.

TABLE 1

| Summary of proteins in vicinity of conserved sequence R-KLEB repeat in *Klebsiella pneumoniae* genome | | |
| --- | --- | --- |
| Category | Genes | Function |
| Pathogenic/Virulence proteins | | |
| Toxins | Protein D (Glycerophosphoryldiesterphosphodiesterase) | Influences in upper respiratory tract |
| | (FebP) iron-enterobactin transporter binding protein | Transporter of enterobactin toxins |
| DNA repair machinery | DNA polymerase IV | Non-targetted mutagenesis |

TABLE 1-continued

Summary of proteins in vicinity of conserved sequence
R-KLEB repeat in *Klebsiella pneumoniae* genome

| Category | Genes | Function |
|---|---|---|
| | Survival proteins | |
| Stress response | CstA | Carbon starvation response |
| Host immune evasion | EutC (ethanolamine ammonia lyase) | Used as an alternative nitrogen source during pathogenesis |
| | Essential Proteins | |
| Essential proteins | nadC | Involved in NAD+ formation |
| | tRNA synthase | Involved in production of tRNA |
| | Alpha-L-arabinofuranosidase | Arabinose metabolism |
| | Sugar transporters | Uptake of glucose and other carbohydrate sources by the bacteria |
| | HutI(Imidazolonepropionase) | Important part in amino acid metabolism |
| | Phophopentomutase | Important part in pentose pathway metabolism and purine metabolism |

TABLE 2

Summary of proteins in vicinity of conserved sequence R-NEIS repeat
in *Neisseria gonorrhoeae* and *Neisseria meningitidis* genomes.

| Category | Genes | Function |
|---|---|---|
| | Pathogenic/Virulence proteins | |
| Toxins | Pilin proteins | Invokes host immune response |
| | PilC | Involved in formation of type IV pilus |
| | TspB2 | T-cell stimulating protein, induces host immune response |
| | Opacity proteins | Involved in an adhesion to epithilial cells |
| DNA repair machinery | DNA polymerase IV | Non-targetted mutagenesis |
| | DNA topoisomerase/Gyrase | Negative supercoiling |
| | Excinuclease | Mismatch repair |
| | Uvr_B | Mismatch repair |
| | Survival proteins | |
| Competence proteins | ComE | Involved in uptake of exogenous DNA |
| Stress response | FrpC | Produced under iron starvation condition |
| | Essential Proteins | |
| Essential proteins | DNA polymerase III | Involved in DNA synthesis |
| | tRNA-synthase | Involved in production of tRNA |
| | Alpha-L-arabinofuranosidase | Arabinose metabolism |
| | Sugar transporters | Uptake of glucose and other carbohydrate sources by the bacteria |

TABLE 3

Summary of proteins in vicinity of conserved sequence
R-SAL repeat in *Salmonella enterica* genome.

| Category | Genes | Function |
| --- | --- | --- |
| Pathogenic/Virulence proteins | | |
| Toxins | RcsB-RcsC | Regulators of toxins |
| | Outer membrane porin protein | Produced during infections for transport of virulence factors |
| | YscW | Regulator of type III secretion system YscC (toxin) |
| | SopD | Involved in induction of diarrhoea symptom |
| Biofilm formation | Queue cluster (C/D) | Queuosine biosynthesis |
| DNA repair machinery | MutH | Mismatch repair protein |
| | DNA topoisomerase | Unwinding supercoiling |
| | Exonuc_VII | Exodeoxyribonuclease activity |
| | Uvr_D | Exonuclease activity |
| Survival proteins | | |
| Stress response | Diadenosinetetraphosphate | Stress response regulator |
| Host immune evasion | Lipopolysachharide O-antigen chain length regulator (Wzz) | Resistance to complement system in human |
| Essential Proteins | | |
| Essential proteins | HisG | Directly control histidine biosynthesis |
| | Sugar transporters | Uptake of glucose and other carbohydrate sources by the bacteria |
| | PTS system proteins | Important part in Glycolysis |
| | PFK | Important part in Glycolysis |

TABLE 4

Summary of proteins in vicinity of conserved sequence
R-YER repeat in *Yersinia pestis* genome.

| Category | Genes | Function |
| --- | --- | --- |
| Pathogenic/Virulence proteins | | |
| Toxins | Adhesion Proteins | Enables pathogen to attach to the host |
| | Heme gene cluster | Iron sequestration in the host |
| | Rhamnose biosynthesis | Enables the production of O-antigen and its export |
| | RelA-spoT | Involved in synthesis of ppGpp molecule that enhances further virulence |
| Host immune response | O-antigen lipopolysaccharide | Antigen present on pathogen cell surface that elicits host immune response |
| | WzyE/WzzE | Elicits host immune response |
| | WecC/WecG | Elicits host immune response |
| | Lipocalin | Elicits host immune response |
| Flagellar protein | FliP/FliR/FlgA | Involved in flagellar biosynthesis that is essential for infection of the host |
| | PilM | Pilus assembly protein - involved in flagellar biosynthesis |
| | MreD | Rod shape determining protein |
| Survival proteins | | |
| Self defence | Insecticidal toxin complex | Toxin against insects such as Hawk moth - true function unknown |
| | Sugar transporters | Uptake of glucose and other carbohydrate sources by the bacteria |
| DNA repair machinery | DNA polymerase | Involved in DNA synthesis during repair |
| | DNA topoisomerase | Involved in unwinding negative supercoiling in DNA |
| | Uvr_D | Helicase involved in exicision repair |
| | MutS/MutH | Involved in DNA mismatch repair |

TABLE 4-continued

Summary of proteins in vicinity of conserved sequence
R-YER repeat in *Yersinia pestis* genome.

| Category | Genes | Function |
|---|---|---|
| | Exonuclease cluster | Involved in cleaving the ends of DNA fragments during repair. |
| Stress response | Cold shock protein | Produced in response to temperature irregularity |
| | Hsp33 like chaperonin | Produced in response to temperature irregularity |
| | Tellurium resistance protein | Produced in response to excess of toxic tellurium uptake |
| Essential Proteins | | |
| | RNA associated proteins | tRNA synthesis, RNA degradation etc. |
| | Quinone/associated molecules, vitamin cofactors | Involved in bacterial electron transport chains |
| | DNA synthesis/ modification | Purine/pyrimidine biosynthesis, DNA methylases, nucleoside kinases etc. |
| | Metabolism of essential metabolites | Gluconate, galactose, succinyl benzoate, alanine, glycine,histidine metabolisms etc. |
| | Cell wall assembly | Bacterial peptidoglycan hydrolases |
| | Signal transduction associated proteins | Rho termination factor, RNA polymerase sigma factor, phosphate kinases, other transcription factors |
| | Transporters | Sugar transporters, |

The identified R-PROTEO nucleotide repeat sequences and their reverse complement can be used to target the genomes of the pathogenic strains of the candidate pathogen as well as the flanking genes (which includes virulence and survival genes) surrounding these R-PROTEO sequences simultaneously and carry out changes like but not limited to gene silencing, gene recombination, gene substitution with a new function etc.

Figures 3A, 3B:
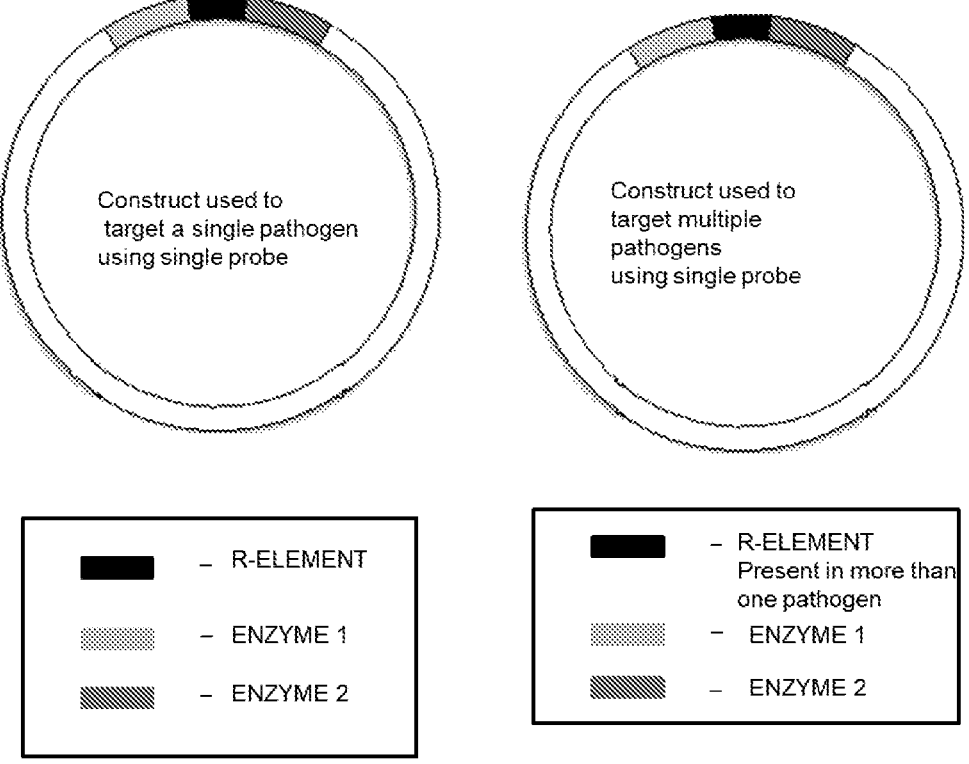
FIGS. 3A, 3B and 3C shows components of a construct containing multiple target sequences capable of combating one or more than one pathogenic infections according to an embodiment of the disclosure.

The targeting method can be of the following types: Type I having Single Probe and Single Pathogen as shown in FIG. 3A. In this type a construct containing single genomic consensus sequence (R-PROTEO) corresponding to nucleotide repeat in a single genus within Proteobacteria and the necessary enzymatic machinery (required for recognizing the R-PROTEO sequence and nicking the bound complex as well as cleaving the flanking genes) is used to target a single candidate pathogen or candidate genus of phylum Proteobacteria. The other features of the engineered polynucleotide construct are similar to those explained for the administration module 122. Type II with Single Probe and Multiple Pathogens as shown in FIG. 3B. In this type an engineered polynucleotide construct containing single consensus nucleotide repeat sequence (R-PROTEO) that is present in the genome of more than one pathogen or more than one genus of phylum Proteobacteria and the necessary enzymatic machinery as described in administration module 122 can be used to simultaneously target those pathogens in which this consensus sequence is present using a single engineered polynucleotide construct. The features of the engineered polynucleotide construct will be similar to those discussed in the administration module.

Figure 3C:
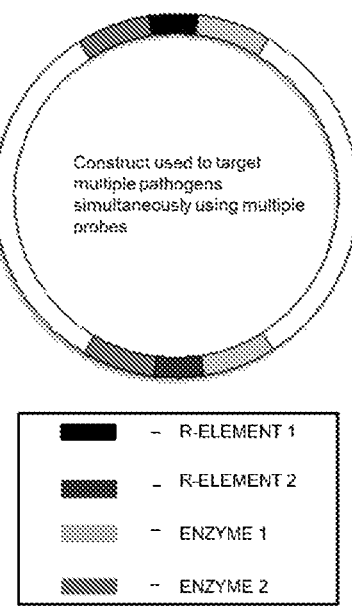

Type III with Multiple Probes and Multiple Pathogens as shown in FIG. 3C. In this type a construct comprising of multiple nucleotide repeat sequences (R-PROTEO) which are cloned into one construct along with the necessary enzymatic machinery can be used to simultaneously target multiple pathogens of phylum Proteobacteria. The features of the engineered polynucleotide construct will be similar to those discussed in the administration module *.

Figure 4:
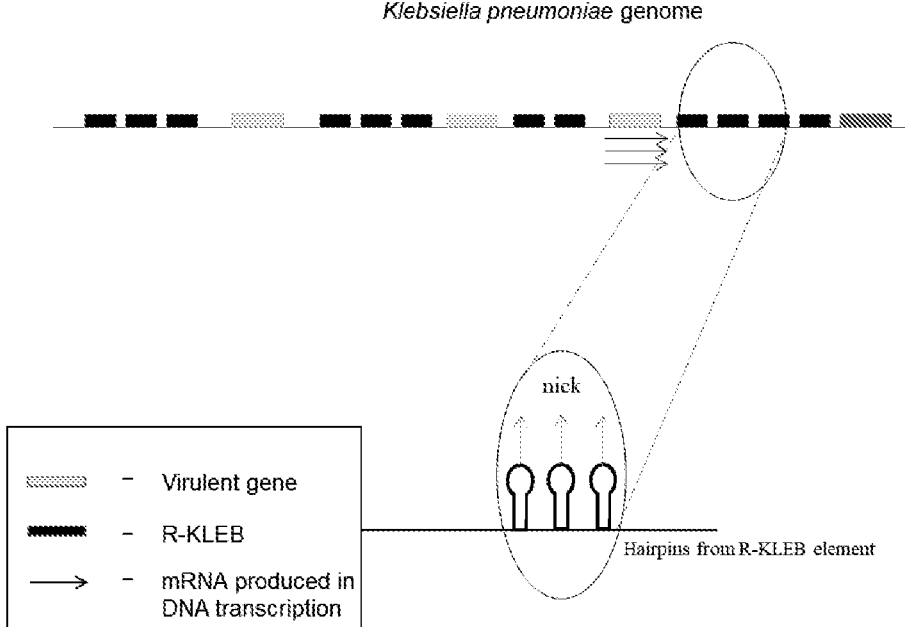
FIG. 4 shows targeting of palindromic and non-palindromic nucleotide repeat sequences in *Klebsiella pneumoniae* genome according to an embodiment of the disclosure.

According to an embodiment of the disclosure, the system 100 further includes the testing module 120 and the administration module 122. The testing module 120 is configured to check the presence of secondary structure formation in the identified set of nucleotide repeat sequence. There could be the presence of the secondary structures such as hairpin loop formation. Depending on the presence of the secondary structure, the administration module 122 is configured to administer an engineered polynucleotide construct to treat the pathogenic infection. The construct works in such a way that it targets multiple regions in the genome simultaneously. A schematic representation of targeting of palindromic and non-palindromic repeat sequences in *Klebsiella pneumoniae* genome is shown in FIG. 4.

In an embodiment the engineered polynucleotide construct may comprise of a circular DNA comprising of an origin of replication. Further the construct may comprise of regulatory elements like a promoter sequence, ribosomal binding site, start codon, a cassette comprising of first and second enzyme flanking the nucleotide repeat sequence or reverse complement of the nucleotide repeat sequence R-PROTEO cloned into the system, stop codons and transcription terminator. The promoter sequence may depend on the pathogen being targeted as well as the regulation required to express the components of the construct at a specific targeted site (for example, within a living being or an infected area). The construct may also be equipped to create a poly A tail in mRNA to stabilize the sequence. The poly A tail refers to a stretch of polynucleotide Adenine nucleotides at the 3' end of mRNA. In one embodiment, the first and second enzyme can be nickase and exonuclease cloned in any order. The target R-PROTEO within the pathogen genome can be recognized and bound by the reverse complement sequence and the complex thus formed can be nicked by the nickase enzyme. The exonuclease can then chop off the duplex formed as well as flanking genes once it recognizes a nick. In another embodiment, the enzymes can be cas9 sequences (may be obtained from *Streptococcus pyogenes*) flanking the R-PROTEO or reverse complement of R-PROTEO which can act as sgRNA (single guide RNA) for the CRISPR-Cas (Clustered Regularly Interspaced Short Palindromic Repeats) system hence obtained. The R-PROTEO or its reverse complement is recognized by the reverse complement sequence or the target R-PROTEO sequence on the polynucleotide construct and is complex formed by the binding of R-PROTEO sequence to its reverse complement. The cas9 may then act as an endonuclease and chop off the nick and flanking sequences. The nucleotide repeat sequence can be targeted by delivering an engineered polynucleotide construct using a bacterial, plasmid or a viral vector to the target bacterial cell. In one embodiment the composition may comprise of: the first element comprising a polynucleotide sequence of CRISPR-Cas system wherein the polynucleotide sequence may comprise a nucleotide repeat sequence (identified nucleotide repeat or its reverse complement) called a guide sequence capable of hybridizing to target sequence (nucleotide repeat sequence on pathogen), a tracr sequence and a tracr mate sequence. The second element may comprise of CRISPR enzyme coding sequences like CAS enzymes. It should be noted that in all these embodiments R-PROTEO sequences can be cloned within same polynucleotide sequence along with a bacterial or viral vector and the other features mentioned above to target more than one pathogen using the same compact construct. Any other construct cassette that may bring about the recognition of the R-PRO-TEO sequences in bacterial genomes and subsequent nicking and chopping of R-PROTEO sequences and the flanking genes is within the scope of this invention. These polynucleotides comprising the nucleotide repeat sequence, the genes encoding enzymes and the other features discussed above can be inserted into laboratory acceptable vectors which allow insertion of external DNA fragments; In one embodiment construct may be carried by vectors like plasmid or phage based cloning vectors. The regulatory elements can be designed according to information available for the pathogen being targeted.

In another embodiment, in addition to the above mentioned features, if bacterial conjugation is to be used as a construct delivery method, the construct may comprise of a relaxase, coding sequences for structural proteins (e.g. pili) and those for regulatory proteins for conjugation. It should be noted that in both embodiments multiple R-PROTEO sequences can be cloned to target more than one pathogen using the same compact construct. Any other construct cassette that may bring about the recognition of the R-PRO-TEO and subsequent chopping of R-PROTEO and the flanking genes is within the scope of this invention.

Depending on the result of testing module 120, there could be two cases as follows:

Case I: If the identified nucleotide repeat sequences R-PROTEO are found to be palindromic the following three strategies may be used. Strategy I: If the R-PRO-TEO is shown to inhibit flanking gene, R-PROTEO is used as target and insert a strong palindromic sequence to ensure the down-regulation of transcription of flanking genes. Palindromic sequences in a transcription bubble form hairpin loops which hinders DNA transcription by stalling the RNA polymerase enzyme thereby down-regulating the flanking gene expression. Strategy II: If the R-PROTEO is shown to promote flanking genes, R-PROTEO is used as target to nick the pathogen genome at multiple locations and cleave the flanking genes. Hairpin loops formed in the mRNA could be involved in prevention of the early decay of mRNA.

Strategy III: If the R-PROTEO is found to be a transcription terminator with a poly A tail following it, R-PRO-TEO is used as target and insert a strong palindromic sequence to ensure the down-regulation of transcription of flanking genes. The presence of a strong terminator region ensures that the gene upstream of it isn't transcribed multiple times as the RNA polymerase falls of at that region. This ensures the down-regulation in the transcription of the flanking genes.

Figure 5:
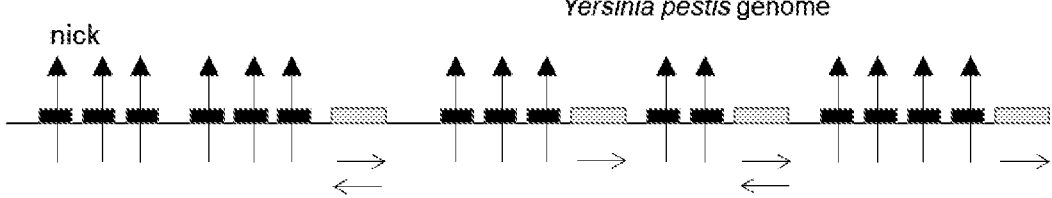
FIG. 5 shows enzymatic cleavage in the *Yersinia pestis* genome according to an embodiment of the disclosure.
Figure 5:
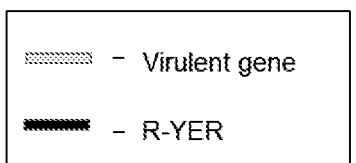

Case II: If the identified nucleotide repeat sequences are not found to be palindromic, the identified repeat sequences (R-PROTEO) are used as target to nick the pathogen genome at multiple locations and cleave the flanking genes. A schematic representation of *Yersinia pestis* genome showing enzymatic cleavage in either directions is shown in FIG. 5.

The administration module 122 can use any pharmaceutically acceptable method of carrying the construct to target the conserved sequences in a pathogen genome. In different embodiments the utility can be, but not limited to oral medicine, topical creams, nasal administration, aerosol sprays, injectable cocktail etc.

In an embodiment, the construct can be administered to the infected site (either living beings or environmental site) through targeted construct delivery methods such as the use of targeted liposomes (wherein, the liposome is tagged with molecules on the external surface that may be specific and functionally important to the candidate genus and the tagged liposome can be used to transfer the construct into the pathogen), targeted nanoparticles (wherein, a targeting molecule that is specific to the candidate genus can be attached to the nanoparticle like but not limited to Ag or Au nanoparticle along with the construct, thereby allowing the tagged nanoparticle to release the construct into the pathogen), phage based delivery method (wherein, the construct can be placed within the phage infecting the candidate genus thereby transferring the construct into pathogen) and bacterial conjugation (wherein, the construct can be placed in other bacteria that can conjugate with the candidate genus and the construct can be transferred to the pathogen through natural conjugation method) etc. In an embodiment, the lipid constitution of the membrane for the targeted liposome can be modified to target specific set of bacteria.

In another embodiment, immunoliposomes can be created with specific antibodies towards ligands of specific pathogen (for example, antibodies against concanavalin A for targeting extracellular matrix of biofilms). The lipid bilayer can be made sensitive to the toxins or other virulence factors of the pathogen in order to release the construct only in infected areas where toxins are present.

In another embodiment, the construct can also be administered to the infected site through non-targeted construct delivery methods such as the use of non-targeted nanoparticles (wherein, nanoparticles can form cages that can hold the construct which are then released into the pathogen), non-targeted liposomes (wherein, the liposomes are phospholipid capsules which can be used to hold the construct that can then merge with the pathogen cell membrane to release the construct inside the pathogen) etc. In an embodiment, attenuated bacteria can also be used to deliver nanoparticles into tissue spaces where they can be released to act upon actual site of infection (as shown in creation of NanoBEADS in a study where *Salmonella* was used to deliver nanoparticles containing a drug to deep tissues). In another example, minicells produced by bacteria can also be used to package the construct and deliver it to specific areas in the infected site. In another embodiment, these delivery methods can be used to target the construct to infected surfaces also. Any other laboratory accepted method of administration of the construct to the infected site is within the scope of this disclosure.

According to an embodiment of the disclosure, the efficacy module 124 is used to assess the efficacy of the treatment methodology described in this disclosure. The efficacy module 124 comprises any laboratory acceptable methods of detecting presence of pathogens present at the infected site. In one embodiment, presence of viable living cells can be detected by utilizing presence of bacterial mRNA which has a short half-life and will not exist once the cells are dead. This mRNA based method may involve identifying antigen/protein specific for the pathogen which can be utilized as a marker for that pathogen and produced by the pathogen in abundance and the corresponding gene on the pathogen genome can be obtained (For e.g. Caf1 gene in Yersinia, invA in Salmonella and cppB in Neisseria gonorrhoeae etc.). The mRNA corresponding to expression of these genes can be detected using techniques like but not limited to polymerase chain reaction (RT-PCR) assays or reverse transcriptase strand displacement amplification (RT-SDA) assays. In another embodiment, expression of proteins identified as specific to these pathogens can be detected using various laboratory accepted methods for protein purification and detection (For e.g. Caf1 gene in Yersinia, invA in Salmonella and cppB in Neisseria gonorrhoeae etc). Chromogenic enzyme assays for a pathogen are also within scope of the invention. Specific metabolites (sugar metabolism in Neisseria gonorrhoeae by rapid non-growth tests) or compounds produced by a pathogen can also be detected (using different laboratory acceptable methods like Mass spectrometry, HPLC-MS, spectrometry-based methods etc.) to ascertain pathogen presence. In other embodiments, the identified antigens (Caf1 gene in Yersinia pestis, invA in Salmonella and cppB in Neisseria gonorrhoeae)/marker sequences can be targeted using methods like nucleic acid amplification tests (NAAT), real time PCR, immunoassays (For e.g. antibodies against Proteins IA and IB in Neisseria gonorrhoeae) etc. as well as specific staining and microscopy techniques and flow cytometry methods of detecting pathogens are also within scope of this invention. PCR or Restriction Fragment Length Polymorphism (RFLP) based detection of 16S rRNA in order to identify pathogens can also be utilized (For e.g. Pace 2NG for detection of Neisseria gonorrhoeae). In one more embodiment, staining methods can also be utilized to identify a pathogen and establish viability of a pathogen cell (e.g. propidium iodide can be used for identifying dead cells). Cell toxicity assays can also be utilized for toxins based detection of pathogens. Further in case of sporulating bacteria, spore detection assays can also be utilized. In case of culturable bacteria, the viability of pathogens can even be established using culturing methods using selective media followed by methods to detect specific pathogens discussed above. In case of an infection in living beings observation of phenotypic effects like alleviation of infection symptoms is also within scope of this disclosure. The symptoms may vary with type of infection and may be observed by registered medical practitioner or healthcare professional. Any other method of detecting pathogens are also within scope of this disclosure. In case pathogen presence is detected, the construct can be administered again using administration module 120 and repeated till pathogen is eliminated.

Figure 6B:
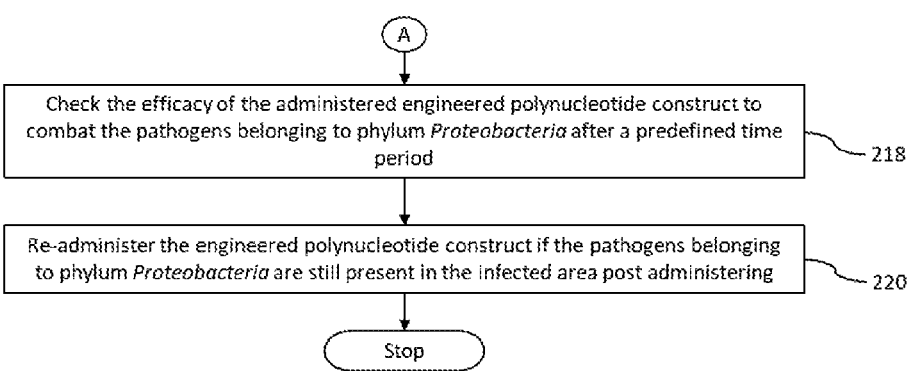

In operation, a flowchart 200 illustrating the steps involved for combating infections due to pathogens belonging to phylum Proteobacteria can be shown in FIG. 6A-6B. Initially at 202, a sample is obtained from an area infected from the pathogens belonging to phylum Proteobacteria. At step 204, DNA is extracted from the sample using the DNA extraction module 106 which is also configured for pathogen detection. At step 206, the extracted DNA is sequenced using the sequencer 108. In the next step 208, the set of nucleotide sequences in the extracted DNA is identified which occur more than a predefined number of times (refers to the number of occurrences of nucleotide repeat sequence on a genome in a dispersed manner and this number might vary with system and pathogen under consideration. Where the minimum value of predefined number is 10) in the pathogens belonging to phylum Proteobacteria. In an example, the identified set of nucleotide sequences may be referred to R-PROTEO. In addition to that, the identified set of nucleotide sequences are not specific to a single strain of the pathogen. At step 210, the set of neighborhood genes present upstream and downstream of the set of nucleotide sequences are identified.

At step 212, the set of neighborhood genes is categorized or annotated according to functional roles of each of neighborhood gene in the pathogens belonging to phylum Proteobacteria. At step 214, the presence of the secondary structure is tested in the set of nucleotide sequences. The set of nucleotide sequences may be palindromic in nature which may result in the formation of hairpin loops.

At step 216, an engineered polynucleotide construct is prepared and administered on the infected area to combat the infections due to the pathogens belonging to phylum Proteobacteria, wherein the engineered polynucleotide construct is comprising:

one or more of a set of nucleotide repeat sequences with multiple copies dispersed in nucleotide sequences of genomes of Proteobacteria, wherein the set of nucleotide repeat sequences comprises one or more of a Sequence ID 001, reverse complement of the Sequence ID 001, Sequence ID 002, reverse complement of the Sequence ID 002, Sequence ID 003, reverse complement of the Sequence ID 003, Sequence ID 004, reverse complement of the Sequence ID 004 and Sequence ID 005, reverse complement of the Sequence ID 005, a first enzyme capable of nicking and cleaving the identified set of nucleotide repeat sequences, and a second enzyme capable of removal of a set of neighborhood genes flanking the set of nucleotide repeat sequences. In another example, the first enzyme is a nicking enzyme and the second enzyme is a cleaving enzyme.

The administration of construct aims at targeting the identified set of nucleotide repeats and removal of flanking genes on genomes of pathogen infecting the area. The construct works in such a way that it targets multiple regions in the pathogenic genome simultaneously. At step 218, the efficacy of the administration module is assessed and in case pathogen presence is detected at the site, administration module can be utilized repetitively till pathogen is eliminated from the site. And finally at step 220, the engineered polynucleotide construct is re-administered if the pathogens belonging to phylum Proteobacteria are still present after checking using efficacy module in the infected area.

According to an embodiment of the disclosure, the system 100 can also be used in combination with various other known methods to effectively treat the pathogenic infection due to pathogens belonging to phylum Proteobacteria. In an example, the method 200 can be used as preventive method. The method can be used in combination with various other antibacterial agents. One implementation would be the use of quorum quenchers along with the construct to tackle the biofilm formation in hospital surfaces. In another example, the method may be used as a therapeutic measure. The method may be used in combination with various other antimicrobial methods. One implementation would be to use the method along with antibiotics and vaccines against essential proteins for therapeutic purposes.

According to an embodiment of the disclosure, the system 100 for combating infections due to pathogens belonging to phylum Proteobacteria can also be explained with the help of following examples using five pathogens *Salmonella enterica, Klebsiella pneumoniae, Neisseria gonorrhoeae, Neisseria meningitides* and *Yersinia pestis*. Repeat elements are identified on sequenced *Salmonella enterica, Klebsiella pneumoniae, Neisseria gonorrhoeae, Neisseria meningitides* and *Yersinia pestis* genomes by taking a sequence stretch of predefined length Rn and searching across their individual genomes for similar sequence stretches as done by several alignment software. In this embodiment, PILER software was used.

The identified nucleotide repeat sequence consensus for *Salmonella enterica, Klebsiella pneumoniae, Neisseria gonorrhoeae, Neisseria meningitidis* and *Yersinia pestis* are as shown below.

```
Salmonella enterica (R-SAL)
(G|C)(G|C)CTGAT(A|G)(A|G)(C|T)(G|A)CTNNGCNTNTCNGGC

CT

Klebsiella pneumoniae (R-KLEB)
GGCCGGGNNNGGCGN(0,10)CGCCNCCCGG

Neisseria gonorrhoeae (R-NEIS)
(G|A)(T|C)CGTCTGN(0,6)TTCAGA(C|T)(G|A)(A|G)C

Neisseria meningitidis (R-NEIS)
(G|A)(T|C)CGTCTGN(0,6)TTCAGA(C|T)(G|A)(A|G)C

Yersinia pestis (R-YER)
GC(CT)GC(CT)TTCC(TC)GN(0,7)G(A|C)(A|G)
``` where N refers to any nucleotide out of A, T, G and C and numeric values in subscripts indicate the range of the number of times a nucleotide or a set of nucleotides is repeated in the sequence.

On further analysis as discussed below, we observe that these conserved nucleotide stretches (as discussed above) are found in the vicinity of highly virulent and, certain essential genes of the above mentioned pathogens (as shown in TABLES 1, 2, 3 & 4). Results of sequence similarity analysis (using BLAST in this embodiment) reveal that these sequences do not show any significant sequence similarity to any other commensal as well as host genome, thereby reducing the possibility of a cross-reactivity. Hence, these nucleotide repeat elements are ideal candidates for the treatment of infections due to pathogens belonging to phylum Proteobacteria such as *Salmonella enterica, Klebsiella pneumoniae, Neisseria gonorrhoeae, Neisseria meningitidis* and *Yersinia pestis* in patients.

Initially, sequence stretches which repeat multiple times are identified on the pathogenic genomes for all strains belonging to phylum Proteobacteria. These are R-SAL, R-KLEB, R-NEIS and R-YER. Conserved nucleotide repeat elements/sequences are identified on *Salmonella enterica,*

*Klebsiella pneumoniae, Neisseria gonorrhoeae, Neisseria meningitidis* and *Yersinia pestis* genomes by taking sequence stretches of predefined length Rn (20-60 in this embodiment in all the cases), keeping the difference in the start position of these stretches as of $Rn_{i+1}$ and $Rn_i$ as 5 nucleotides. In this implementation, stretches of nucleotide sequences are aligned within the genome by local alignment (as implemented in PILER software) to find the location of consensus nucleotide repeat sequences in all sequenced *Salmonella enterica, Klebsiella pneumoniae, Neisseria gonorrhoeae, Neisseria meningitidis* and *Yersinia pestis* genomes. Sequence based search utilizing any other alignment or repeat finding tools can also be utilized for this purpose.

In the next step, the neighborhood genes of nucleotide repeat elements/sequences are identified and annotated. On each *Salmonella enterica, Klebsiella pneumoniae, Neisseria gonorrhoeae, Neisseria meningitidis* and *Yersinia pestis* genomes where nucleotide repeat elements occur, 10 flanking genes both upstream and downstream are found on each strand (+10 and −10) of DNA. Functional annotations of these genes are performed using HMM search with PFAM as the database. In other embodiments, databases like CDD, SMART etc. can be utilized. Functional categorizations of these genes on the basis of pathways they are involved in are carried out using literature mining. The broad categories have been discussed in TABLES 1, 2, 3 & 4.

The identified nucleotide repeat sequences are then checked for potential secondary structure formation such as hairpin loops. It is seen that R-SAL, R-KLEB and R-NEIS do form a potential hairpin loop.

The R-SAL, R-KLEB and R-NEIS nucleotide repeat element sequences are palindromic and may form a hairpin loop structure indicating their role in regulation of transcription. These loops may either form at DNA level or at the ends of their mRNA during DNA transcription. This hairpin loop in the mRNA could be involved in prevention of the early decay of mRNA, resulting in higher protein formation of the virulence genes which are in the vicinity of these palindromic elements. Reduction in pathogenicity can be achieved by decreasing the stability of mRNA corresponding to these virulent genes which can be attained by removing the hairpin loops. If hairpin loop formation takes place at DNA level it might regulate DNA supercoiling.

Finally, the nucleotide repeat sequence can be targeted using one or more strategy depending on the case 1 or case 2 as discussed above.

According to an embodiment of the disclosure, the number of occurrences and locations of repeats in the strains from *Salmonella enterica, Klebsiella pneumoniae, Neisseria meningitidis* and *Yersinia pestis* are shown below. Due the large number of available strain, only few are provided below:

Salmonella_enterica_subsp._enterica_serovar_Saint-paul_str._SARA26_-_ GCA_000486165.2_ASM48616v2 42 [(40588, 40616), (55321, 55349), (357849, 357877), (365707, 365735), (383084, 383112), (410327, 410355), (891833, 891861), (912464, 912492), (951445, 951473), (1037505, 1037533), (1198993, 1199021), (1295589, 1295617), (1393805, 1393833), (1409821, 1409849), (1439275, 1439303), (1465957, 1465985), (1498916, 1498944), (1519378, 1519406), (1585469, 1585497), (1807598, 1807626), (3080384, 3080412), (3181450, 3181478), (3379686, 3379714), (3644570, 3644598), (3826048, 3826076), (3826101, 3826129), (3826154, 3826182), (3826207, 3826235), (3826260, 3826288), (3870235, 3870263), (3937733, 3937761), (3943397, 3943425), (4036915, 4036943), (4233422, 4233450), (4242095, 4242123), (4244950, 4244978), (4306831, 4306859), (4349268, 4349296), (4392668, 4392696), (4457792, 4457820), (4529470, 4529498), (4674544, 4674572)]

*Salmonella_enterica_subsp._enterica_serovar_Bre-deney_str._CFSAN001080_-_GCA_000487775.2_ASM48777v2* 41 [(110836, 110864), (284321, 284349), (288922, 288950), (353811, 353839), (378892, 378920), (1669686, 1669714), (1876343, 1876371), (1946951, 1946979), (1967417, 1967445), (2000377, 2000405), (2028238, 2028266), (2057609, 2057637), (2067298, 2067326), (2071858, 2071886), (2256703, 2256731), (2408023, 2408051), (2491516, 2491544), (2531779, 2531807), (2930084, 2930112), (3021872, 3021900), (3049000, 3049028), (3066365, 3066393), (3107914, 3107942), (3370555, 3370583), (3435247, 3435275), (3578992, 3579020), (3649390, 3649418), (3722934, 3722962), (3765237, 3765265), (3798864, 3798892), (3874065, 3874093), (4082925, 4082953), (4130511, 4130539), (4138297, 4138325), (4169711, 4169739), (4175375, 4175403), (4248624, 4248652), (4292930, 4292958), (4292983, 4293011), (4293036, 4293064), (4473881, 4473909)]

*Salmonella_enterica_subsp._enterica_sero-var_Typhi_1554-sc-2165329_-_GCA_900205255.1_1554* 41 [(37747, 37775), (52469, 52497), (313092, 313120), (344684, 344712), (352544, 352572), (369921, 369949), (396824, 396852), (486930, 486958), (629028, 629056), (874689, 874717), (888821, 888849), (936632, 936660), (1017988, 1018016), (1384699, 1384727), (1409370, 1409398), (1576493, 1576521), (1579099, 1579127), (1583700, 1583728), (1670525, 1670553), (2936515, 2936543), (3156039, 3156067), (3227399, 3227427), (3306920, 3306948), (3336500, 3336528), (3443972, 3444000), (3540308, 3540336), (3555593, 3555621), (3731950, 3731978), (3775920, 3775948), (3848972, 3849000), (3897141, 3897169), (3961514, 3961542), (4271872, 4271900), (4336408, 4336436), (4347069, 4347097), (4371880, 4371908), (4378582, 4378610), (4590737, 4590765), (4662314, 4662342), (4704366, 4704394), (4753389, 4753417)]

*Klebsiella_pneumoniae_-_GCA_001936035.1_ASM193603v1* No. of occur-rences of R-KLEB: 71 [(385674, 385703), (385875, 385904), (862169, 862197), (868026, 868054), (1181259, 1181288), (1608090, 1608118), (1608206, 1608234), (1608554, 1608582), (1608670, 1608698), (1608786, 1608814), (1608902, 1608930), (1624705, 1624732), (1988312, 1988340), (2139558, 2139586), (2285456, 2285485), (2285546, 2285575), (2329859, 2329887), (2329971, 2330000), (2330088, 2330117), (2330498, 2330526), (2350536, 2350565), (2565436, 2565464), (2565576, 2565604), (2565857, 2565885), (2590068, 2590097), (2590278, 2590307), (2590513, 2590542), (2591135, 2591163), (2620515, 2620544), (2622738, 2622766), (2645747, 2645775), (2652341, 2652369), (2694718, 2694746), (2702888, 2702917), (2703052, 2703081), (2703215, 2703244), (2866114, 2866143), (2875683, 2875712), (2876216, 2876245), (2894168, 2894196), (2894285, 2894313), (2894522, 2894550), (2894640, 2894668), (2894758, 2894786), (2894876, 2894904), (2894994, 2895022), (2955242, 2955271), (2984190, 2984218), (3156645, 3156673), (3156839, 3156867), (3372902, 3372931), (3373015, 3373043), (3373502, 3373531), (3476408, 3476436), (3605277, 3605306), (3660990, 3661019), (3734370, 3734398), (3734808, 3734836), (3735246, 3735274), (3735361, 3735389), (3735476, 3735504), (3735895, 3735923), (3967784, 3967812), (4108206, 4108235), (4108325, 4108354), (4289023, 4289052), (4289162, 4289190), (4546913, 4546941), (4781670, 4781698), (4838117, 4838145), (4875801, 4875830)]

*Klebsiella_pneumoniae_HK787_-_GCA_000813205.1_ASM81320v1* No. of occurrences of R-KLEB: 69 [(29326, 29355), (94142, 94171), (325072, 325100), (330929, 330957), (1617238, 1617267), (1654803, 1654831), (1711248, 1711276), (1760274, 1760302), (2008608, 2008636), (2246667, 2246696), (2432030, 2432059), (2433579, 2433608), (2433694, 2433723), (2433813, 2433841), (2433930, 2433959), (2434049, 2434078), (2434168, 2434197), (2796191, 2796219), (2796623, 2796651), (2864561, 2864590), (2921288, 2921317), (3016262, 3016290), (3124121, 3124150), (3124609, 3124638), (3124722, 3124751), (3125332, 3125361), (3125445, 3125474), (3299567, 3299595), (3469810, 3469838), (3559850, 3559878), (3559969, 3559997), (3560087, 3560115), (3560205, 3560234), (3560429, 3560457), (3561996, 3562024), (3579829, 3579858), (3579884, 3579913), (3580368, 3580397), (3591385, 3591414), (3754039, 3754068), (3762210, 3762238), (3804468, 3804496), (3815026, 3815054), (3815513, 3815541), (3815630, 3815658), (3816040, 3816068), (3847984, 3848013), (3877486, 3877515), (3877604, 3877633), (3878024, 3878053), (3901953, 3901981), (3902094, 3902122), (3902235, 3902263), (4161674, 4161703), (4181708, 4181736), (4181820, 4181848), (4181938, 4181966), (4182280, 4182308), (4182690, 4182718), (4182807, 4182835), (4236027, 4236056), (4236117, 4236146), (4236207, 4236236), (4382099, 4382127), (4521203, 4521231), (4878905, 4878933), (4879029, 4879057), (4892452, 4892480), (4908255, 4908283)]

*Neisseria_meningitidis_M04-240196_-_GCA_000191505.1_ASM19150v1* No. of occurrences of R-NEIS: 77 [(7427, 7450), (73410, 73433), (74017, 74041), (80525, 80547), (94752, 94776), (137258, 137276), (151840, 151862), (177359, 177383), (182450, 182474), (184582, 184606), (196541, 196562), (207425, 207448), (310038, 310062), (322710, 322733), (338702, 338726), (362813, 362836), (411259, 411282), (463386, 463408), (465086, 465108), (481755, 481779), (490600, 490624), (498097, 498120), (537076, 537099), (617787, 617811), (620929, 620952), (627263, 627286), (636489, 636511), (644333, 644356), (702341, 702365), (791288, 791311), (794481, 794504), (825686, 825710), (825817, 825841), (829389, 829412), (861523, 861547), (907827, 907849), (955704, 955727), (992133, 992156), (1067149, 1067168), (1079146, 1079169), (1121338, 1121362), (1210982, 1211006), (1219698, 1219722), (1229508, 1229532), (1236576, 1236598), (1252086, 1252110), (1298648, 1298671), (1306192, 1306216), (1319013, 1319037), (1352306, 1352328), (1355658, 1355681), (1362676, 1362697), (1372932, 1372953), (1433996, 1434018), (1470028, 1470051), (1510524, 1510547), (1530574, 1530596), (1670507, 1670529), (1693439, 1693461), (1707901, 1707923), (1727164, 1727187), (1850826, 1850849), (1869369, 1869392), (1871830, 1871854), (1873002, 1873026), (1890788, 1890809), (1898715, 1898737), (1953010, 1953034), (1991522, 1991545), (2006357, 2006379), (2011385, 2011408), (2012737, 2012760), (2055873, 2055897), (2122020, 2122042), (2157969, 2157992), (2172951, 2172974), (2229259, 2229282)]

*Neisseria_meningitidis_WUE_2594_-_* GCA_000253215.1_ASM25321v1 No. of occurrences of R-NEIS: 77

[(7546, 7569), (94791, 94814), (110909, 110932), (151740, 151762), (187964, 187986), (215428, 215452), (220213, 220236), (269042, 269065), (275787, 275809), (290462, 290485), (333296, 333319), (387446, 387468), (396109, 396131), (415749, 415773), (418220, 418243), (424832, 424855), (425056, 425079), (484665, 484688), (504839, 504861), (516619, 516641), (548977, 548999), (561154, 561177), (681227, 681249), (701125, 701148), (741147, 741170), (776192, 776214), (838776, 838799), (841324, 841346), (845549, 845572), (888373, 888397), (931605, 931628), (947699, 947722), (1001124, 1001145), (1047350, 1047374), (1080552, 1080575), (1111485, 1111509), (1118240, 1118262), (1133462, 1133486), (1234477, 1234500), (1283234, 1283256), (1354440, 1354463), (1360016, 1360040), (1363585, 1363609), (1363716, 1363740), (1375969, 1375991), (1390760, 1390783), (1425851, 1425874), (1474773, 1474797), (1535137, 1535160), (1582204, 1582226), (1591410, 1591433), (1597744, 1597767), (1600818, 1600842), (1602216, 1602240), (1680806, 1680829), (1720019, 1720042), (1727804, 1727828), (1728200, 1728224), (1751206, 1751228), (1752239, 1752261), (1804404, 1804427), (1851968, 1851991), (1869263, 1869285), (1895024, 1895046), (1918891, 1918915), (1934419, 1934442), (1946828, 1946850), (2057619, 2057642), (2067996, 2068019), (2079906, 2079930), (2082037, 2082060), (2087923, 2087947), (2116024, 2116046), (2165174, 2165198), (2176845, 2176867), (2183352, 2183376), (2183959, 2183982)]

*Neisseria_meningitidis_alpha710_-_* GCA_000152165.1_ASM15216v1 No. of occurrences of R-NEIS: 75 [(8588, 8611), (62590, 62613), (66467, 66490), (67074, 67098), (80458, 80480), (144848, 144870), (171605, 171629), (178828, 178852), (190879, 190900), (201394, 201417), (307967, 307991), (320430, 320453), (335741, 335765), (358356, 358379), (402682, 402705), (451749, 451772), (456578, 456600), (457868, 457890), (474782, 474806), (481337, 481361), (490228, 490251), (564710, 564733), (585149, 585171), (599812, 599834), (632406, 632429), (766695, 766717), (786751, 786774), (858663, 858686), (914937, 914958), (925194, 925215), (930697, 930720), (958585, 958608), (961777, 961800), (974422, 974444), (987071, 987095), (991133, 991157), (1015993, 1016016), (1028738, 1028761), (1042625, 1042648), (1127823, 1127847), (1160703, 1160726), (1190614, 1190638), (1197371, 1197393), (1212595, 1212619), (1274252, 1274275), (1312261, 1312284), (1359387, 1359409), (1465425, 1465448), (1472987, 1473011), (1486827, 1486851), (1520573, 1520595), (1549624, 1549647), (1599979, 1600003), (1655736, 1655759), (1664543, 1664565), (1673748, 1673771), (1680084, 1680107), (1683225, 1683249), (1683703, 1683727), (1765608, 1765631), (1848352, 1848375), (1854968, 1854991), (1857438, 1857462), (1875550, 1875571), (1887049, 1887071), (1940584, 1940608), (1978338, 1978361), (1993073, 1993095), (1998981, 1999004), (2000333, 2000356), (2052485, 2052509), (2119045, 2119067), (2156529, 2156552), (2172465, 2172488), (2221553, 2221576)]

*Yersinia_pestis_biovar_Microtus_str._91001_GCA_000007885.1_ASM788v1* No. of occurrences of R-YER: 37

[(154451, 154472), (170214, 170235), (334550, 334571), (490461, 490482), (511777, 511798), (569987, 570008), (743487, 743508), (1103676, 1103697), (1362723, 1362744), (1382303, 1382324), (1420431, 1420450), (1593537, 1593558), (1754860, 1754881), (1967349, 1967370), (2209303, 2209324), (2242245, 2242266), (2345172, 2345193), (2404216, 2404237), (2514897, 2514918), (2523820, 2523841), (2605410, 2605431), (2761036, 2761057), (2796044, 2796066), (2834458, 2834479), (2839579, 2839596), (2876312, 2876333), (2876436, 2876457), (2930596, 2930617), (2985333, 2985354), (3178959, 3178980), (3548009, 3548030), (3554362, 3554383), (4002153, 4002174), (4106324, 4106345), (4195190, 4195211), (4377808, 4377829), (4424042, 4424063)]

*Yersinia_pestis_CO92_-_* GCA_000009065.1_ASM906v1 No. of occurrences of R-YER: 37

[(153725, 153746), (169488, 169509), (309469, 309490), (330771, 330792), (389671, 389692), (530538, 530559), (871741, 871762), (1001366, 1001387), (1018413, 1018434), (1281166, 1281187), (1453631, 1453650), (1491774, 1491795), (1513271, 1513292), (1766626, 1766647), (1808843, 1808864), (1871107, 1871128), (2034164, 2034185), (2463435, 2463456), (2496387, 2496408), (2606699, 2606720), (2667705, 2667726), (2753896, 2753917), (2841330, 2841351), (3013458, 3013479), (3048449, 3048471), (3154680, 3154701), (3233248, 3233265), (3238380, 3238401), (3316899, 3316920), (3317023, 3317044), (3372068, 3372089), (3614809, 3614830), (3756626, 3756647), (4080975, 4080996), (4127186, 4127207), (4335188, 4335209), (4341473, 4341494)]

*Yersinia_pestis_CO92_-_* GCA_001293415.1_ASM129341v1 No. of occurrences of R-YER: 37

[(86681, 86702), (174115, 174136), (260307, 260328), (321313, 321334), (431623, 431644), (464576, 464597), (793046, 793067), (956106, 956127), (1018370, 1018391), (1060587, 1060608), (1313941, 1313962), (1335438, 1335459), (1373583, 1373602), (1546757, 1546778), (1809518, 1809539), (1826565, 1826586), (1956193, 1956214), (2297391, 2297412), (2438258, 2438279), (2497158, 2497179), (2518460, 2518481), (2658440, 2658461), (2674203, 2674224), (3142140, 3142161), (3148425, 3148446), (3356429, 3356450), (3402640, 3402661), (3726991, 3727012), (3869521, 3869542), (4112263, 4112284), (4167308, 4167329), (4167432, 4167453), (4245951, 4245972), (4251087, 4251104), (4329651, 4329672), (4435898, 4435920), (4470890, 4470911)]

The embodiments of present disclosure herein provides a method and system for combating infections due to pathogens belonging to phylum Proteobacteria.

The embodiments of present disclosure herein provides a method and system for combating infections due to Proteobacteria.

Sequences and their reverse complements have been disclosed:

Sequence 001: *Salmonella enterica* (R-SAL)
(G|C)(G|C)CTGAT(A|G)(A|G)(C|T)(G|A)CTNNGCNTNTCNGGC

CT

Sequence 002: *Klebsiella pneumoniae* (R-KLEB)
GGCCGGGNNNGGCGN$_{(0,10)}$CGCCNCCCGG Sequence 003: *Neisseria gonorrhoeae* (R-NEIS)
(G|A)(T|C)CGTCTGN$_{(0,6)}$TTCAGA(C|T)(G|A)(A|G)C Sequence 004: *Neisseria meningitidis* (R-NEIS)
(G|A)(T|C)CGTCTGN$_{(0,6)}$TTCAGA(C|T)(G|A)(A|G)C Sequence 005: *Yersinia pestis* (R-YER)
GC(C|T)GC(C|T)TTCC(T|C)GN$_{(0,7)}$G(A|C)(A|G)

where N refers to any nucleotide out of A, T, G and C and numeric values in subscripts indicate the range of the number of times a nucleotide or a set of nucleotides is repeated in the sequence The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of developing resistance against the various pathogens belonging to phylum Proteobacteria. The embodiment provides a system and method for combating infections due to pathogens belonging to phylum Proteobacteria It is to be understood that the scope of the protection is extended to such a program and in addition to a computer-readable means having a message therein; such computer-readable storage means contain program-code means for implementation of one or more steps of the method, when the program runs on a server. The hardware device can be any kind of device which can be programmed including e.g. any kind of computer like a server or a personal computer, or the like, or any combination thereof. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, BLU-RAYs, flash drives, disks, and any other known physical storage media. It is intended that the disclosure and examples be considered as exemplary only, with a true scope and spirit of disclosed embodiments being indicated by the following claims.

---

The invention claimed is:

1. A method for combating infections due to pathogens belonging to phylum Proteobacteria, the method comprising:

obtaining a sample from an infected area;

isolating and extracting DNA from the obtained sample using one of laboratory methods;

detecting presence of the pathogens belonging to phylum Proteobacteria from the obtained sample using a plurality of pathogen detection methods;

sequencing the isolated DNA using a sequencer;

identifying, via one or more hardware processors, a set of nucleotide repeat sequences in the sequenced DNA which are occurring more than a predefined number of times in the pathogens belonging to phylum Proteobacteria;

identifying, via the one or more hardware processors, a set of neighborhood genes present upstream and downstream of the set of nucleotide repeat sequences;

annotating, via the one or more hardware processors, the set of neighborhood genes according to their functional roles in their respective pathogens based on their involvement in pathways in the identified set of neighborhood genes;

testing, via the one or more hardware processors, the presence of a secondary structure in the identified set of nucleotide repeat sequences;

preparing and administering an engineered polynucleotide construct on the infected area to combat the infections due to the pathogens belonging to phylum Proteobacteria, wherein the engineered polynucleotide construct is comprising:

one or more of the set of nucleotide repeat sequences identified and selected with multiple copies dispersed in nucleotide sequences of genomes of one or more of Salmonella enterica, Klebsiella pneumoniae, Neisseria gonorrhoeae, Neisseria meningitides and Yersinia pestis, wherein the set of nucleotide repeat sequences comprises one or more of a SEQ ID NO: 001, reverse complement of the SEQ ID NO: 001, SEQ ID NO: 002, reverse complement of the SEQ ID NO: 002, SEQ ID NO: 003, SEQ ID NO: 003, reverse complement of the SEQ ID NO: 003, SEQ ID NO: 004, reverse complement of the SEQ ID NO: 004 and SEQ ID NO: 005, reverse complement of the SEQ ID NO: 005, a first enzyme capable of nicking and cleaving the identified set of nucleotide repeat sequences, and a second enzyme capable of removal of one or more members of the set of neighborhood genes flanking the set of nucleotide repeat sequences;

checking the efficacy of the administered engineered polynucleotide construct to combat the pathogens belonging to phylum Proteobacteria after a predefined time period, and re-administering the engineered polynucleotide construct if the pathogens belonging to phylum Proteobacteria are still present in the infected area post administering.

2. The method of claim 1, wherein the sample obtained from infected area is one or more of fecal matter, blood, urine, tissue biopsy, hospital surfaces or environmental samples.

3. The method of claim 1, wherein the DNA isolation and extraction methods comprise of laboratory standardized protocols including DNA isolation and extraction kits.

4. The method of claim 1, wherein the plurality of pathogen detection methods comprises one or more of:

a sequencing technique, a flow cytometry based methodology, a microscopic examination of the microbes in collected sample, a microbial culture of pathogens in vitro, immunoassays, cell toxicity assay, enzymatic, colorimetric or fluorescence assays, assays involving spectroscopic/spectrometric/chromatographic identification and screening of signals from complex microbial populations.

5. The method of claim 1, wherein the pathogen detection also comprise of one or more of sequenced microbial DNA data, a microscopic imaging data, a flow cytometry cellular measurement data, a colony count and cellular phenotypic data of microbes grown in in-vitro cultures, immunological data, proteomic/metabolomics data, and a signal intensity data.

6. The method of claim 1, further comprising sequenced microbial data, wherein the sequenced microbial data comprises sequences obtained from sequencing platforms comprising sequences of marker genes including 16S rRNA, Whole Genome Shotgun (WGS) sequences, sequences obtained from a fragment library based sequencing technique, sequences from a mate-pair library or a paired-end library based sequencing technique, a complete sequence of pathogen genome or a combination thereof, wherein, the pathogen detection in the sample depends on identification of taxonomic groups from these sequences.

7. The method of claim 1, wherein the engineered polynucleotide construct is inserted into vectors which allow insertion of external DNA fragments, wherein the construct is carried by plasmid or phage based cloning vectors, wherein the engineered polynucleotide construct further comprise of bacteria specific promoter sequence, a terminator sequence, a stretch of Thymine nucleotides which is transcribed into a polyA tail for stabilizing the mRNAs transcripts corresponding to each enzyme, wherein the promoters and terminators specific to candidate bacteria can be utilized in the construct.

8. The method of claim 1, wherein the engineered polynucleotide construct comprises a CRISPR-Cas system, comprising:

a CRISPR enzyme, a guide sequence capable of hybridizing to the identified target nucleotide repeat sequence within the pathogen genome, a tracr mate sequence, and a tracr sequence, wherein the guide sequence, the tracr mate and the tracr sequences are linked to one regulatory element of the construct while the CRISPR enzyme is linked to another regulatory module within the vector.

9. The method of according to claim 1, wherein the engineered polynucleotide construct is administered using one or more of following delivery methods: liposome encompassing the engineered polynucleotide construct, targeted liposome with a ligand specific to the target pathogen on the external surface and encompassing the engineered polynucleotide construct to be administered, using nanoparticles such as Ag and Au, gene guns or micro-projectiles where the construct is adsorbed or covalently linked to heavy metals which carry it to different bacterial cells, or bacterial conjugation methods and bacteriophage specific to the targeted pathogen.

10. The method of according to claim 1, wherein the first enzyme is a nicking enzyme and the second enzyme is a cleaving enzyme.

11. The method of according to claim 1, wherein the set of nucleotide repeat sequences are found in multiple copies at distant locations on the genomes of all pathogenic strains of candidate genus or species and these nucleotide repeat sequences do not show more than two nucleotide sequence similarity based match to genome sequences corresponding to genera or species other than the genome sequences of pathogens belonging to the candidate genus or species or with genomes of commensal strains within the candidate genus or species; wherein distant locations refer to distance of greater than 10000 nucleotide base pairs.

12. The method of claim 1, further comprising the step identifying the set of nucleotide sequences comprises:

selecting a nucleotide sequence stretches from the genomes of strains of candidate pathogen of a predefined length Rn with a difference in the start position of consecutive nucleotide stretches Rni+i and Rni as 5 nucleotides, wherein the predefined length refers to the length of a stretch of nucleotide sequence picked from the complete nucleotide sequence of a bacterial genome, used as a seed input for local sequence alignment tools, aligning a stretch of sequences with the candidate bacterial genome using a local alignment tool to find the location of the set of nucleotide repeat sequences in genomes of pathogen belonging to phylum Proteobacteria, and identifying the set of nucleotide repeat sequences, repeating more than 10 times at distant locations on the bacterial genome as the set of nucleotide repeat sequences, wherein the set of nucleotide repeat sequences with repeats comprising of one or more of a SEQ ID NO: 001, a SEQ ID NO: 002, a SEQ ID NO: 003, a Sequence-SEQ ID NO: 004, a sequence SEQ ID NO: 005, reverse complement of the SEQ ID NO: 001, reverse complement of the SEQ ID NO: 002, reverse complement of the SEQ ID NO: 003, reverse complement of the SEQ ID NO: 004 or reverse complement of the SEQ ID NO: 005.

13. The method of claim 1, wherein the identified nucleotide repeat sequences are in genomic neighborhood of or flanking the genes encoding proteins with essential functions within a pathogen genome, wherein the genomic neighborhood refers to regions lying within a predefined number of genes to the selected nucleotide repeat sequence or the reverse complement of the selected nucleotide repeat sequence on the candidate pathogen genome or lying within a distance of predefined number of bases with respect to the selected nucleotide repeat sequence on the genome of the pathogen wherein, the important functional genes refer to the genes in pathogens which encode for proteins which are critical for survival, pathogenicity, interaction with the host, adherence to the host or for the virulence of bacteria, wherein the minimum predefined number of genes to be considered in genomic neighborhood is 10.

14. The method of claim 11, wherein the distant locations refer to distance of greater than 10000 nucleotide base pairs and wherein the sequence matching is performed by processor implemented tools for nucleotide sequence alignment which comprise PILER, BLAST or Burrows wheeler alignment tool.

15. The method of claim 1, with an additional step of analyzing the obtained sample for non-culturable taxonomic groups or pathogens by amplification of marker genes like 16S rRNA within bacteria.

16. The method of claim 1, with an additional step of analyzing the obtained sample for non-culturable taxonomic groups or pathogens by the binning of whole genome sequencing reads into various taxonomic groups using different methods including sequence similarities as well as several methods using supervised and unsupervised classifiers for taxonomic binning of metagenomics sequences.

17. A method for combating infections due to pathogens belonging to phylum Proteobacteria, the method comprising:

obtaining a sample from an infected area;

isolating and extracting DNA from the obtained sample using one of a laboratory methods;

sequencing the isolated DNA;

detecting, via one or more hardware processors, presence of the pathogens belonging to phylum Proteobacteria using a plurality of detection methods, wherein the pathogens belonging to phylum Proteobacteria comprise one or more of *Salmonella enterica, Klebsiella pneumoniae, Neisseria gonorrhoeae, Neisseria meningitides* and *Yersinia pestis* from the isolated DNA of the sample;

preparing and administering an engineered polynucleotide construct on the infected area to combat the infections due to the pathogens belonging to phylum Proteobacteria, wherein the engineered polynucleotide construct is comprising:

one or more of a set of nucleotide repeat sequences identified and selected with multiple copies at dispersed locations on the candidate pathogen genomes of one or more of the one or more of *Salmonella enterica, Klebsiella pneumoniae, Neisseria gonorrhoeae, Neisseria meningitides* and *Yersinia pestis* genomes, wherein the set of nucleotide repeat sequences comprises one or more of a SEQ ID NO: 001, a SEQ ID NO: 002, a SEQ ID NO: 003, a SEQ ID NO: 004, a sequence SEQ ID NO: 005, reverse complement of the SEQ ID NO: 001, reverse complement of the SEQ ID NO: 002, reverse complement of the SEQ ID NO: 003, reverse complement of the SEQ ID NO: 004 or reverse complement of the SEQ ID NO: 005, a first enzyme capable of nicking and cleaving the identified set of nucleotide sequences, and a second enzyme capable of removal of a set of neighborhood genes flanking the set of nucleotide repeat sequences;

checking the efficacy of the administered engineered polynucleotide construct to combat the pathogens belonging to phylum Proteobacteria after a predefined time period, and re-administering the engineered polynucleotide construct if the pathogens belonging to phylum Proteobacteria are still present in the infected area post administering.

18. A system for combating infections due to pathogens belonging to phylum Proteobacteria, the system comprises:

a sample collection module for obtaining a sample from an infected area;

a pathogen detection and DNA extraction module isolating DNA from the obtained sample using one of a laboratory methods;

a sequencer for sequencing the isolated DNA;

one or more hardware processors;

a memory in communication with the one or more hardware processors, wherein the one or more first hardware processors are configured to execute programmed instructions stored in the one or more first memories, to:

identify a set of nucleotide repeat sequences in the sequenced DNA which are occurring more than a predefined number of times in the pathogens belonging to phylum Proteobacteria;

identify a set of neighborhood genes present upstream and downstream of the set of nucleotide repeat sequences;

annotate the set of neighborhood genes according to their functional roles in their respective pathogen based on their involvement in pathways in the identified set of neighborhood genes;

test the presence of a secondary structure in the identified set of nucleotide repeat sequences;

an administration module for preparing and administering an engineered polynucleotide construct on the infected area to combat the infections due to the pathogens belonging to phylum Proteobacteria, wherein the engineered polynucleotide construct is comprising:

one or more of a set of nucleotide repeat sequences identified and selected with multiple copies dispersed in nucleotide sequences of genomes of one or more of *Salmonella enterica, Klebsiella pneumoniae, Neisseria gonorrhoeae, Neisseria meningitides* and *Yersinia pestis*, wherein the set of nucleotide repeat sequences comprises one or more of a SEQ ID NO: 001, reverse complement of the SEQ ID NO: 001, SEQ ID NO: 002, reverse complement of the SEQ ID NO: 002, SEQ ID NO: 003, reverse complement of the SEQ ID NO: 003, SEQ ID NO: 004, reverse complement of the SEQ ID NO: 004 and SEQ ID NO: 005, reverse complement of the SEQ ID NO: 005, a first enzyme capable of nicking and cleaving the identified set of nucleotide repeat sequences, and a second enzyme capable of removal of one or more members of the set of neighborhood genes flanking the set of nucleotide repeat sequences; and an efficacy module for checking the efficacy of the administered engineered polynucleotide construct to combat the pathogens belonging to phylum Proteobacteria after a predefined time period, and re-administer the engineered polynucleotide construct if the pathogens belonging to phylum Proteobacteria are still present in the infected area post administering.

19. One or more non-transitory machine readable information storage mediums comprising one or more instructions which when executed by one or more hardware processors cause a method for combating infections due to pathogens belonging to phylum Proteobacteria, the method comprising:

obtaining a sample from an infected area;

isolating and extracting DNA from the obtained sample using one of laboratory methods;

sequencing the isolated DNA using a sequencer;

identifying, via one or more hardware processors, a set of nucleotide repeat sequences in the sequenced DNA which are occurring more than a predefined number of times in the pathogens belonging to phylum Proteobacteria, identifying, via the one or more hardware processors, a set of neighborhood genes present upstream and downstream of the set of nucleotide repeat sequences;

annotating, via the one or more hardware processors, the set of neighborhood genes according to their functional roles in their respective pathogens based on their involvement in pathways in the identified set of neighborhood genes;

testing, via the one or more hardware processors, the presence of a secondary structure in the identified set of nucleotide repeat sequences;

preparing and administering an engineered polynucleotide construct on the infected area to combat the infections due to the pathogens belonging to phylum Proteobacteria, wherein the engineered polynucleotide construct is comprising:

one or more of the set of nucleotide repeat sequences identified and selected with multiple copies dispersed in nucleotide sequences of genomes of one or more of *Salmonella enterica, Klebsiella pneumoniae, Neisseria gonorrhoeae, Neisseria meningitides* and *Yersinia pestis*, wherein the set of nucleotide repeat sequences comprises one or more of a SEQ ID NO: 001, reverse complement of the SEQ ID NO: 001, SEQ ID NO: 002, reverse complement of the SEQ ID NO: 002, SEQ ID NO: 003, reverse complement of the SEQ ID NO: 003, SEQ ID NO: 004, reverse complement of the SEQ ID NO: 004 and SEQ ID NO: 005, reverse complement of the SEQ ID NO: 005, a first enzyme capable of nicking and cleaving the identified set of nucleotide repeat sequences, and a second enzyme capable of removal of one or more
    members of the set of neighborhood genes flanking
    the set of nucleotide repeat sequences;

checking the efficacy of the administered engineered
    polynucleotide construct to combat the pathogens 5
    belonging to phylum Proteobacteria after a predefined
    time period, and re-administering the engineered polynucleotide construct
    if the pathogens belonging to phylum Proteobacteria
    are still present in the infected area post administering. 10

\* \* \* \* \*